US012806211B2

(12) United States Patent
Leng

(10) Patent No.: US 12,806,211 B2
(45) Date of Patent: Nov. 24, 2026

(54) METHODS OF TREATING PAIN AND DEPRESSION

(71) Applicant: MOREHOUSE SCHOOL OF MEDICINE, Atlanta, GA (US)

(72) Inventor: Tiandong Leng, Snellville, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 418 days.

(21) Appl. No.: 18/497,105

(22) Filed: Oct. 30, 2023

(65) Prior Publication Data

US 2024/0165129 A1 May 23, 2024

Related U.S. Application Data

(60) Provisional application No. 63/381,970, filed on Nov. 2, 2022.

(51) Int. Cl.

*A61K 31/575* (2006.01)
*A61P 25/04* (2006.01)
*A61P 25/24* (2006.01)

(52) U.S. Cl.

CPC ............ *A61K 31/575* (2013.01); *A61P 25/04* (2018.01); *A61P 25/24* (2018.01)

(58) Field of Classification Search

CPC ......... A61K 31/575; A61P 25/04; A61P 25/24
See application file for complete search history.

(56) References Cited

U.S. PATENT DOCUMENTS 4,522,811 A 6/1985 Eppstein et al.
2018/0311182 A1 11/2018 Nathan et al.

FOREIGN PATENT DOCUMENTS

WO WO-2021144720 A1 * 7/2021 .............. A61P 25/28

OTHER PUBLICATIONS

International Search Report and Written Opinion Filed in International Application PCT/US23/78148 mailed on Apr. 11, 2024.

Porsolt, R., Le Pichon, M. & Jalfre, M. Depression: a new animal model sensitive to antidepressant treatments. Nature 266, 730-732 (1977).

Petit-Demouliere, B., Chenu. F. & Bourin, M. Forced swimming test in mice a review of antidepressant activity. Psychopharmacology 177, 245-255 (2005).

Cryan JF, Mombereau C, Vassout A. The tail suspension test as a model for assessing antidepressant activity: review of pharmacological and genetic studies in mice. Neurosci BioBehav Rev. 2005; 29 (4-5): 571-625.

Li X, Tizzano JP, Griffey K, Clay M, Lindstrom T, Skolnick P. Antidepressant-like actions of an AMPA receptor potentiator (LY392098). Neuropharmacology. Jun. 2001;40(8). 1028-33.

Bechtholt-Gompf AJ, Walther HV, Adams MA, Carlezon WA Jr, OngOr D, Cohen BM. Blockade of astrocytic glutamate uptake in rats induces signs of anhedonia and impaired spatial memory. Neuropsychopharmacology, Sep. 2010,35 (10) 2049-59.

Stephanie C. Dulawa, Rene Hen, Recent advances in animal models of chronic antidepressant effects: The novelty-induced hypophagia test, Neuroscience & Biobehavioral Reviews, vol. 29, Issues 4-5, 2005, pp. 771-783.

Robert J Blanchard, Chnstlna R McKittrick, D.Caroline Blanchard, Animal models of social stress: effects on behavior and brain neurochemical systems, Physiology & Behavior, vol. 73, Issue 3, 2001, pp. 261-271.

N.N. Kudryavtseva, I.V. Bakshtanovskaya, L.A. Koryakina, Social model of depression in mice of C57BU6J strain, Pharmacology Biochemistry and Behavior, vol. 38, Issue 2, 1991, pp. 315-320.

Christina Kurre Nielsen, Jorn Amt, Connie Sanchez, Intracranial self-stimulation and sucrose intake differ as hedonic measures following chronic mild stress interstrain and interindividual differences, Behavioural Bram Research, vol. 107, Issues 1-2, 2000, pp. 21-33.

Holmes A. Targeted gene mutation approaches to the study of anxiety-like behavior m mice. Neurosci Biobehav Rev. May 2001,25(3) 261-73.

* cited by examiner

*Primary Examiner* — Samantha L Shterengarts
*Assistant Examiner* — Ernesto Valle
(74) *Attorney, Agent, or Firm* — Ping Wang; Kalos Athena Wang PLLC

(57) ABSTRACT

The present application relates to a method of treating pain, comprising: administering a therapeutically effective amount of triol to a subject to reduce symptoms of pain. The present application also relates to a method of treating depression, comprising: administering a therapeutically effective amount of triol to a subject to reduce symptoms of depression. The cholesterol metabolite, cholestane-3β, 5α, 6β-triol (Triol), inhibits ASICs in a subunit-dependent manner. It inhibits homomeric ASIC1a and ASIC3, and heteromeric ASIC1a/2a and ASIC1a/2b channels. The inhibition on ASIC1a is use-dependent and voltage-independent.

7 Claims, 28 Drawing Sheets

D

E

F

C

Triol

Cholesterol 5a, 6a-epoxy-Chol

5ß, 6ß–epoxy-Chol

Andro-triol

D

E

F

C

D

E

F

G

H

I

J

A

B

C

D

E

METHODS OF TREATING PAIN AND DEPRESSION

This application claims priority from U.S. Provisional Application No. 63/381,970, filed Nov. 2, 2022, which is herein incorporated by reference.

This invention was made with government support under R01NS128018 and SC3 GM122593 awarded by the National Institute of Health. The government has certain rights in the invention.

FIELD

This application is generally related to treatment of pain, depression, as well as other conditions associated with acidosis.

BACKGROUND

Depression remains one of the most disabling medical diseases but the molecular pathways underlying depression are poorly understood, and existing treatments are too often ineffective. Although current therapies reduce depression, they fail to resolve symptoms completely in as many as 50% of cases. Remission rates are even worse for those who have failed initial medication trials. Thus, novel treatments are critically needed.

The causes of depression and the mechanisms of action of antidepressants remain unclear. Nevertheless, several advances provide a foundation for current understanding of neuroanatomical and neurochemical factors in mood regulation. Multiple brain regions have been implicated, including prefrontal cortex, cingulate, striatum, thalamus, and limbic structures. The amygdala is interconnected with many of these regions and well positioned to play a central role in mood regulation. Given that the amygdala is also critical for anxiety, it is notable that depression is frequently accompanied by anxiety and panic.

Acid-sensing ion channels (ASICs), members of the degenerin/epithelial sodium channel (Deg/ENaC) superfamily, are predominantly expressed in the central and peripheral nervous systems. Six ASIC subunits, including ASIC1a, ASIC1b, ASIC2a, ASIC2b, ASIC3, and ASIC4, have been identified. All ASIC subunits except ASIC2b and ASIC4 can form homomeric channels. Three identical or different subunits assemble to form homotrimeric or heterotrimeric channels. ASICs have been shown to play important roles in several physiological processes, including synaptic transmission and plasticity, learning, and memory, and in pathological conditions such as depression and pain.

ASIC channels are expressed at key pain-related sites in the peripheral nervous system (PNS), the central nervous system (CNS) and in non-neuronal cells. In the PNS, ASIC subunits are expressed in primary afferent fibers. Many of these ASIC-expressing neurons are nociceptive, as defined by the expression of substance P and/or the calcitonin gene-related peptide. Early immunohistochemical studies that identified ASIC1a in substance P-containing neurons of the dorsal root ganglion (DRG) supported the initial enthusiasm for the hypothesis that ASICs mediate nociception. Shortly after ASIC1a was identified, ASIC3 was also discovered, and was determined to be localized to primary afferent nociceptive fibers innervating the skin, muscles, joints and viscera.

ASIC1a is required for acid-evoked currents in central neurons, where it contributes to synaptic plasticity and in the regulation of dendritic spines. ASIC la is expressed widely in the central and peripheral nervous systems and is robustly expressed in structures associated with mood including the amygdala. Consistent with this pattern of localization, disrupting ASIC1a attenuates amygdala activity and ASIC1a knock-out mice exhibit deficits in conditioned and unconditioned fear. Conversely, overexpressing ASIC1a in transgenic mice increased fear conditioning. Therefore, ASIC1a inhibition can evoke behavioral change.

There is a need for improved methods of treating depression and/or pain, and related conditions.

SUMMARY

One of ordinary skill will understand that the differing embodiments disclosed in this application can all be used either independently or in combination with each other and there is no limitation implied on such combinations by the order or manner in which embodiments are disclosed.

An aspect of the application is a method of treating or reducing pain in a subject in need thereof comprising administering to a subject in need thereof a therapeutically effective amount of a pharmaceutical composition comprising triol, or analog compound of triol, or variant of triol with a generic substitution in its chemical structure, and a pharmaceutically acceptable carrier.

An aspect of the application is a method of treating or reducing depression in a subject in need thereof comprising administering to a subject in need thereof a therapeutically effective amount of a pharmaceutical composition comprising triol, or analog compound of triol, or variant of triol with a generic substitution in its chemical structure, and a pharmaceutically acceptable carrier.

Another aspect of the application is a method of treating headaches, comprising: administering a subject in need a therapeutically effective amount of a composition comprises triol.

Another aspect of the application is a kit for treating pain by the method described herein. Another aspect of the application is a kit for treating depression by the method described herein. Another aspect of the application is a kit for treating headaches by the method described herein.

BRIEF DESCRIPTION OF THE DRAWINGS

While the present disclosure will now be described in detail, and it is done so in connection with the illustrative embodiments, it is not limited by the particular embodiments illustrated in the figures and the appended numbered paragraphs.

DETAILED DESCRIPTION

Figure 1:
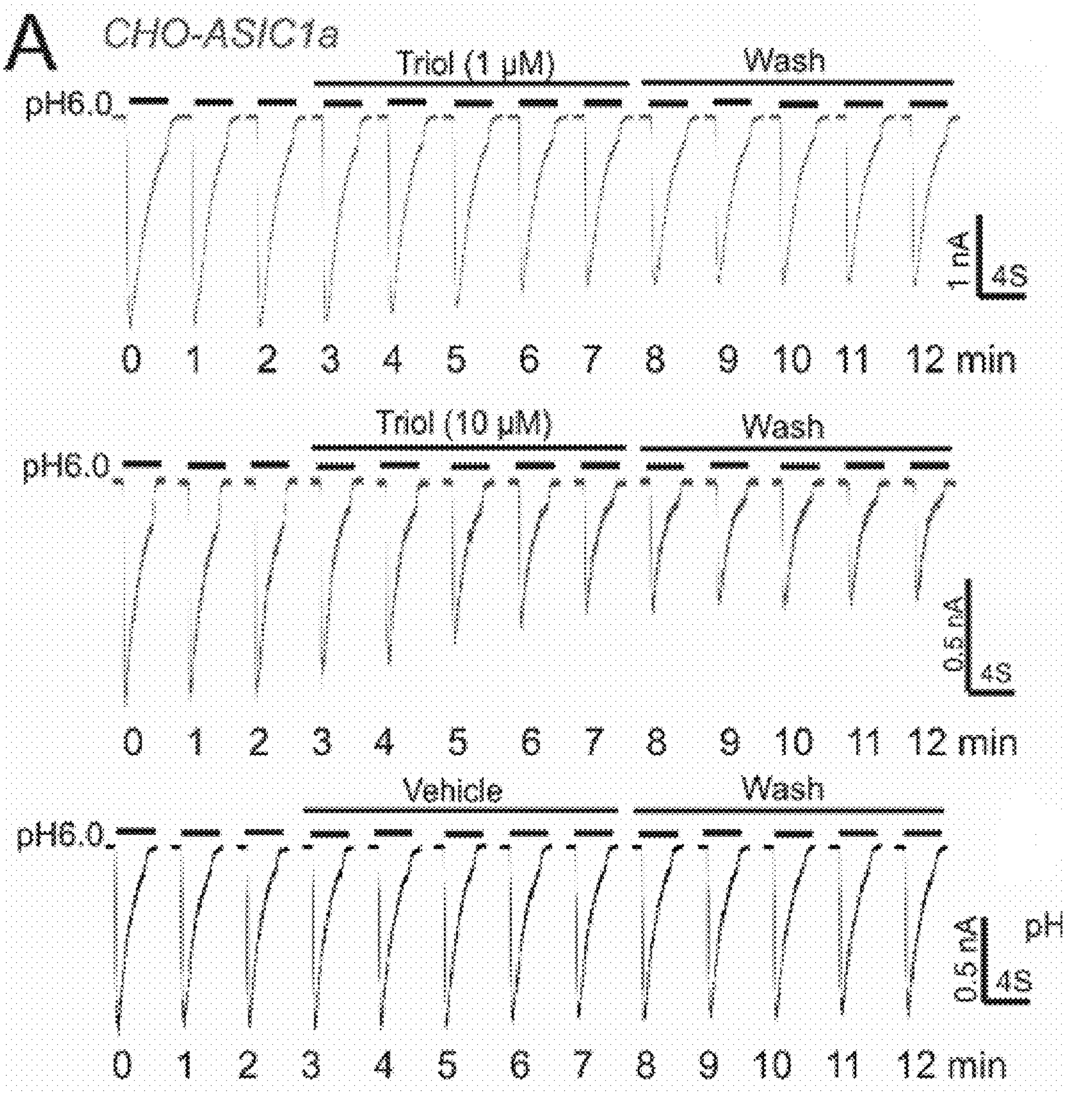
FIG. 1 shows subunit-dependent inhibition of ASICs by Triol in CHO cells. (A) Representative current traces showing the change of ASIC1a currents in the presence of Triol (1 and 10 μM) and vehicle as indicated in CHO-ASIC1a stable cell line. ASIC1a currents were induced by dropping the extracellular pH from 7.4 to 6.0. Triol or vehicle was applied after three stable current traces were obtained. (B) Summary data showing the change of ASIC1a peak currents over time in the presence or absence of Triol (n=5, *p<0.05, p<0.01 compared with vehicle, and #p<0.01, ##p<0.01 compared with 1 μM of Triol at the same time point, two-way ANOVA). (C-D) Representative current traces and summary data showing the effect of Triol (10 μM) on ASIC1β and ASIC2a currents in CHO cells with transient expression of ASIC1β (CHO-ASIC1β) and ASIC2a (CHO-ASIC2a), respectively. ASIC1β and ASIC2a currents were induced by pH drop from 7.4 to 6.0 and 4.5 respectively (n=4-5). (E) Current traces and summary data showing the change of ASIC3 currents in the presence of Triol (10 μM) and vehicle. ASIC3 currents were induced by pH drop from 7.4 to 5.5. (F) Summary data showing the change of ASIC3 peak currents and the sustained current components over time in the presence of vehicle or Triol (n=4-5, p<0.01, compared with vehicle, two-way ANOVA).
Figure 1:
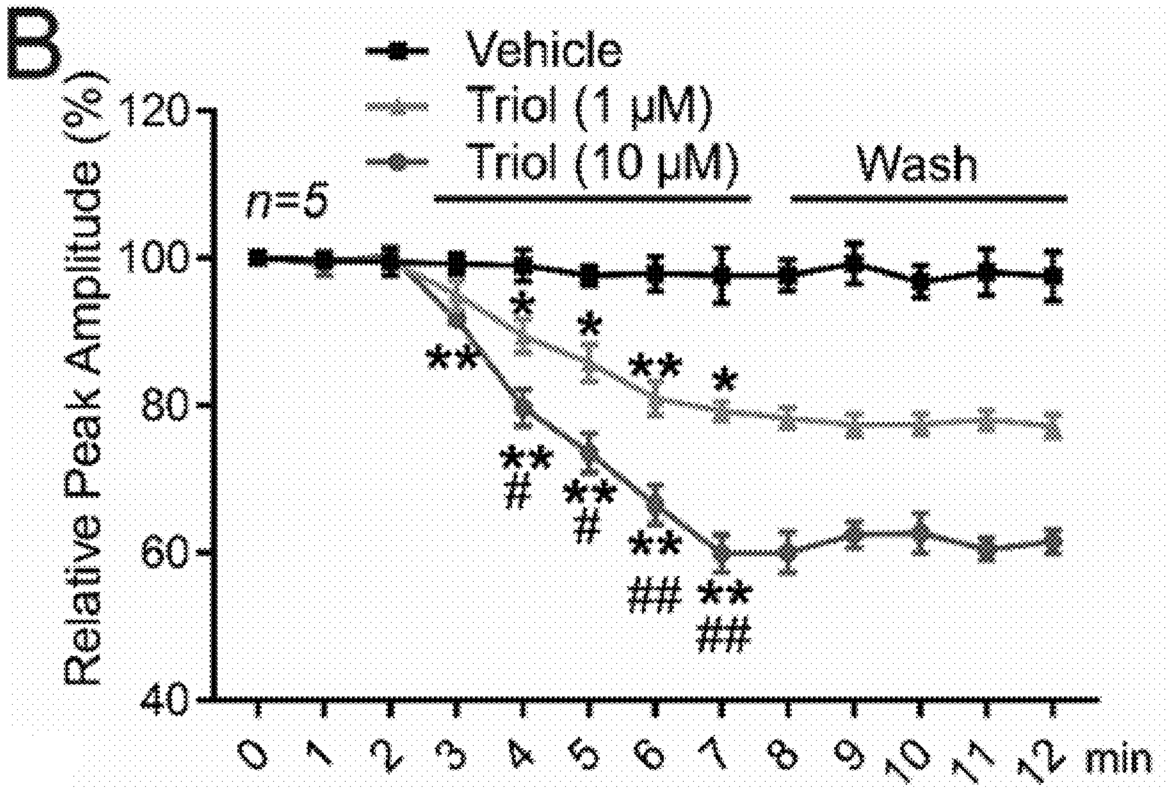
Figure 1:
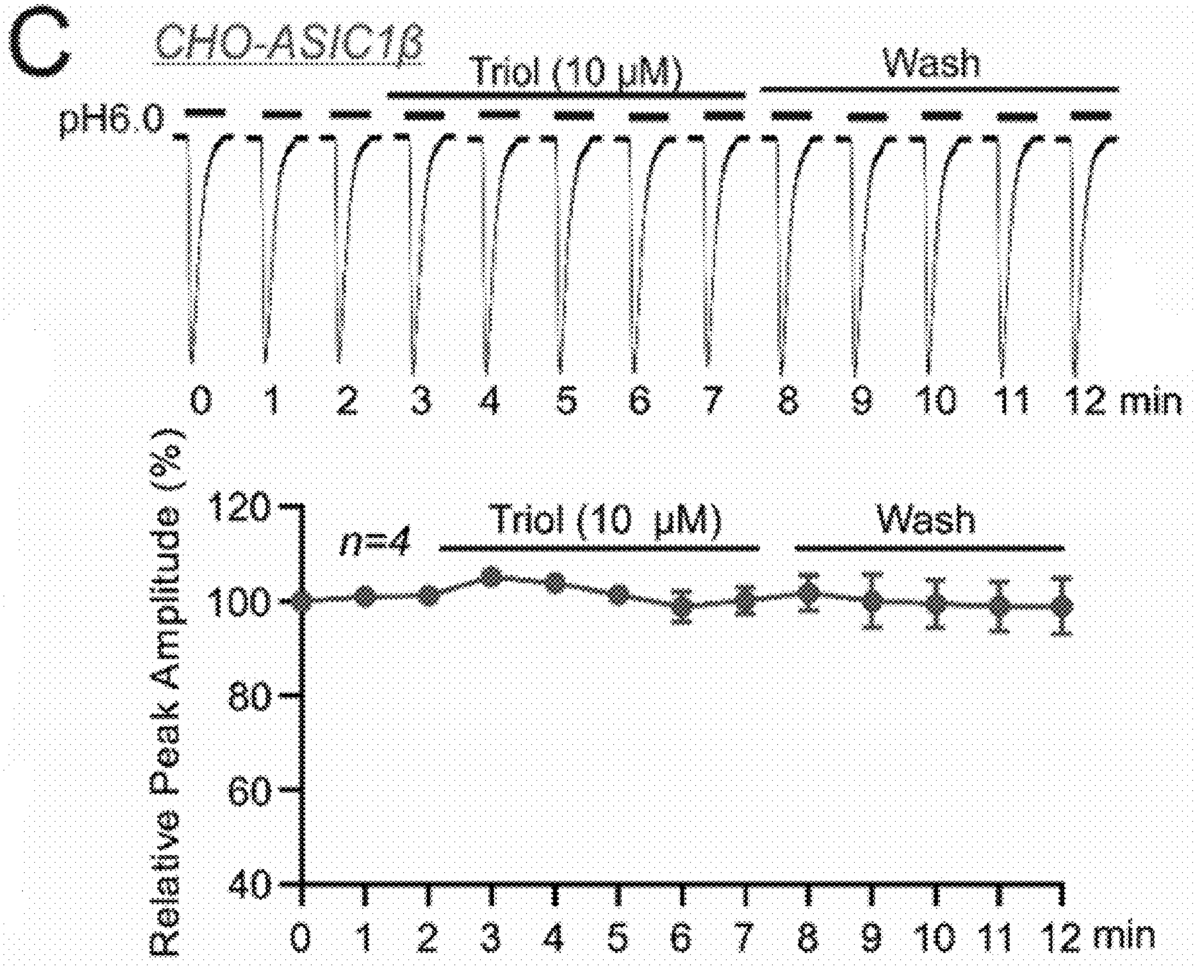
Figure 1:
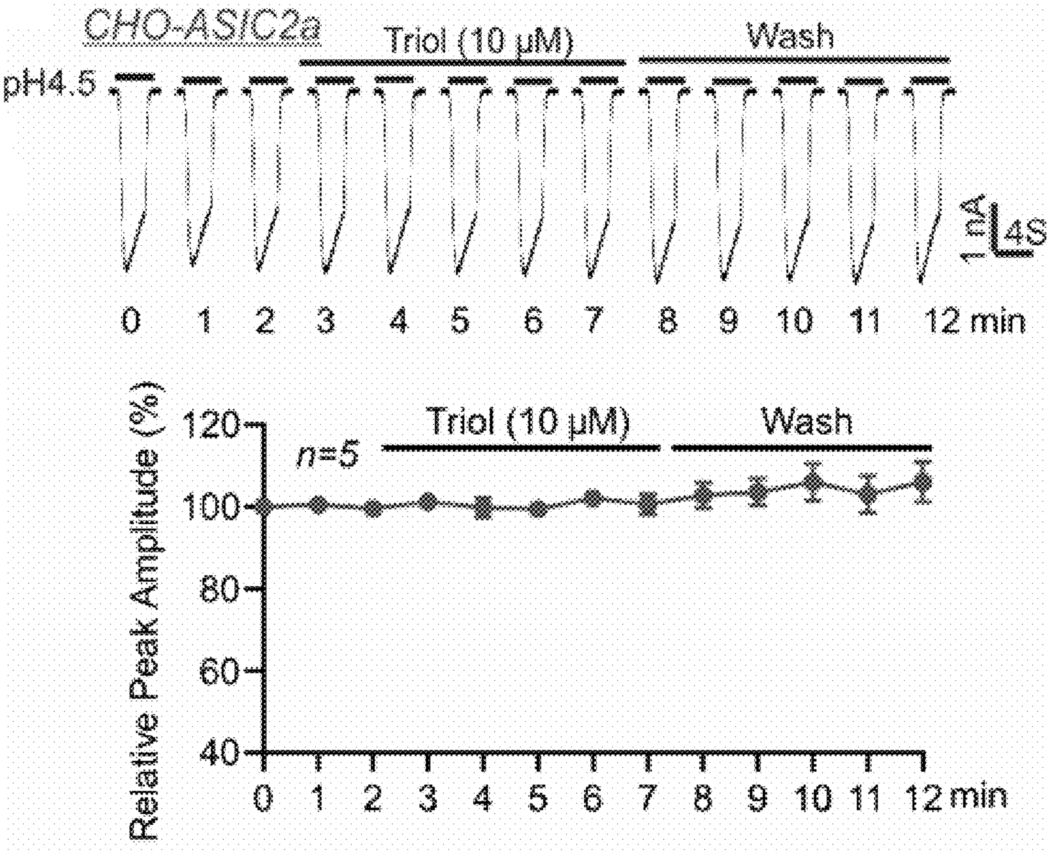
Figure 1:
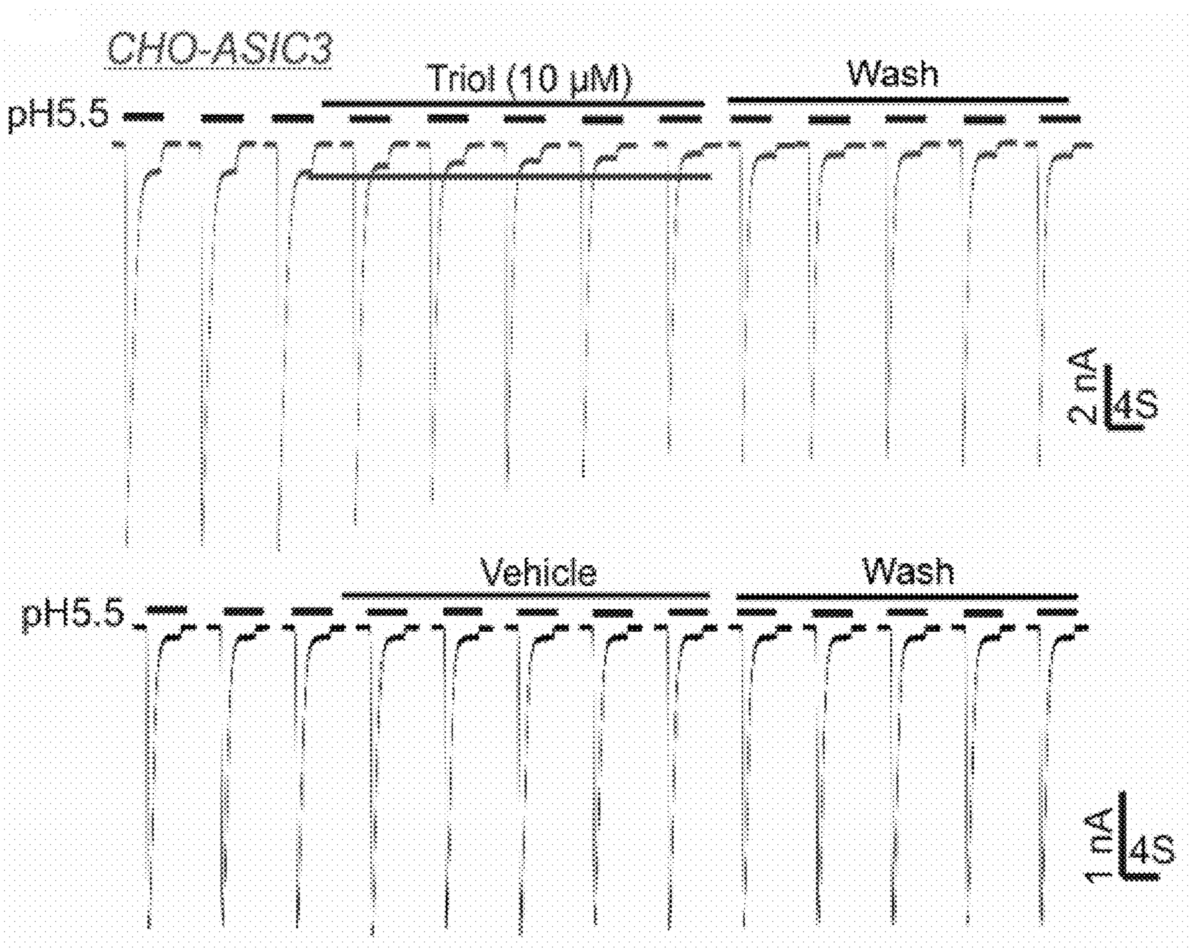
Figure 1:
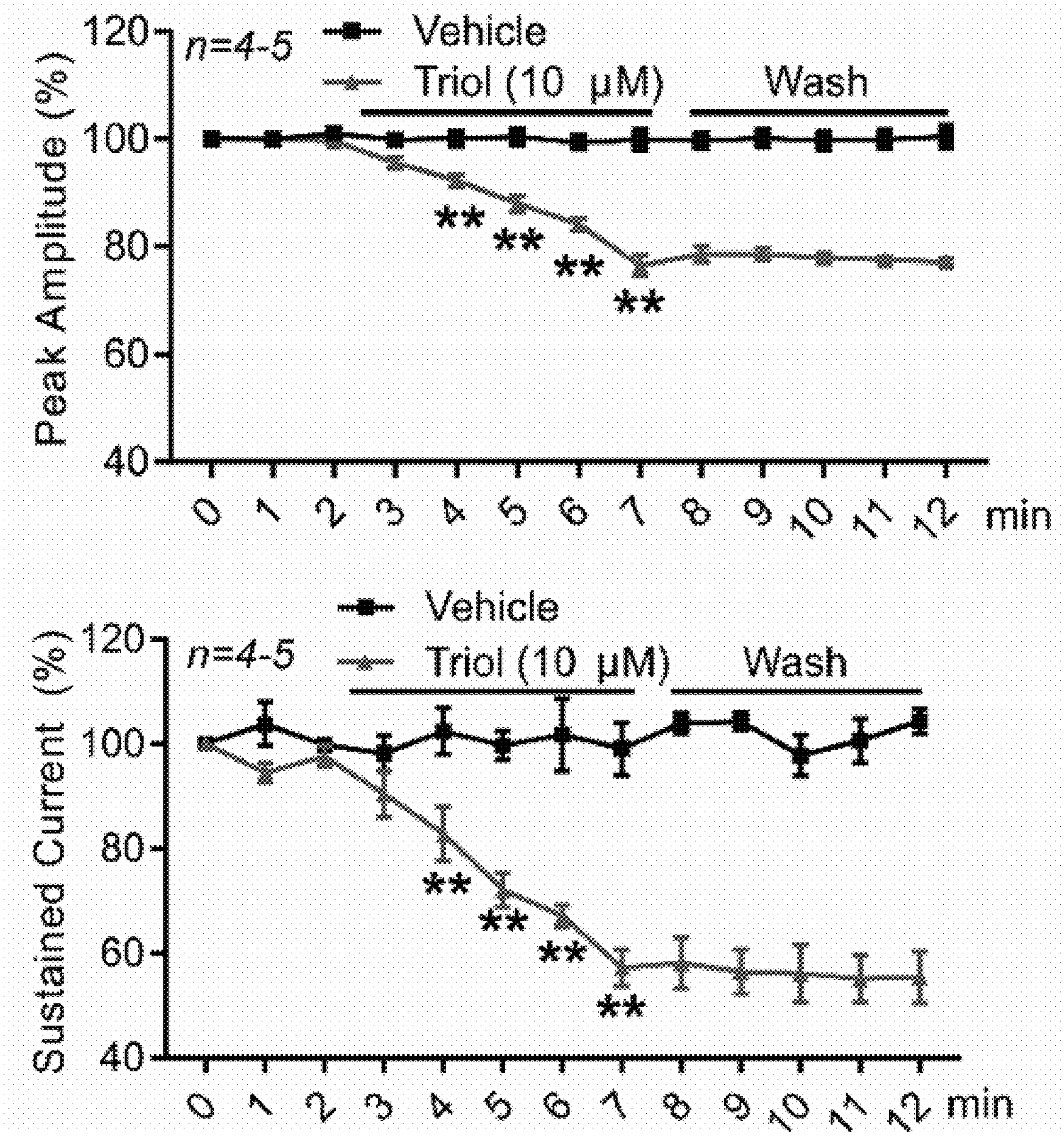

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

I. Definitions

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10"

is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

"Patient" or "subject" as used herein means a mammalian animal, including a human, a veterinary or farm animal, a domestic animal or pet, and animals normally used for clinical research. In one embodiment, the subject of these methods and compositions is a human. In another embodiment, the subject is a female.

The terms "treat," "treating" or "treatment" as used herein, refers to a method of alleviating or abrogating a disorder and/or its attendant symptoms. Th term "reduce," or "reducing" means to lower the intensity or degree of the symptoms of a disorder. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

The term "inhibits" is a relative term, an agent inhibits a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

The term "increased level" refers to a level that is higher than a normal or control level customarily defined or used in the relevant art. For example, an increased level of immunostaining in a tissue is a level of immunostaining that would be considered higher than the level of immunostaining in a control tissue by a person of ordinary skill in the art.

The term "decreased level" refers to a level that is lower than a normal or control level customarily defined or used in the relevant art. For example, a decreased level of immunostaining in a tissue is a level of immunostaining that would be considered lower than the level of immunostaining in a control tissue by a person of ordinary skill in the art.

"Depression" is a mood disorder that causes a persistent feeling of sadness and loss of interest in activities that one used to enjoy. It is a common and serious medical illness that negatively affects how one feels, thinks, and behaves. Symptoms of depression include persistent feelings of sadness, hopelessness, irritability, and fatigue, as well as difficulty concentrating and making decisions. Depression can be related to an anxiety disorder, an obsessive-compulsive disorder, a unipolar disorder or a bipolar disorder. Depression can also lead to physical symptoms such as headaches, stomachaches, and back pain. An increased level of depression means the number and/or severity of physical or emotional symptoms of depression has increased. A decreased level of depression means the number and/or severity of physical or emotional symptoms of depression has decreased. Prevention of depression means that the symptoms of depression do not emerge, or are of reduced severity in an individual at risk of depression in comparison to the severity of such symptoms either observed in control individuals, or previously observed in that at-risk individual.

Symptoms of depression in non-human animal models include, for example, reduced escape-related behavior, anxiety and stress. Tests for depression and/or anxiety and/or stress are the forced swimming test (FST) (eg, Porsolt et al. (1977) Nature 266: 730; and Petit-Demouliere, et al. (2005) Psychopharmacology 177: 245); tail suspension test (see, eg, Cryan et al. (2005) Neurosci. Behay. Rev. 29: 571; and Li et al. (2001) Neuropharmacol. 40: 1028); conditions Place-of-place preference (see, eg, Bechtholt-Gompf et al. (2010) Neuropsychopharmacol. 35: 2049); New appetite reduction trial (Dulawa, et al. (2005) Neurosci. Biobehay. Rev. 29: 771) Social defeat stress test (see, eg, Blanchard et al. (2001) Physiol Behay. 73: 261-271; and Kudryavtseva et al. (1991) Pharmacol. Biochem. Behay. 38: 315); sucrose preference test (For example, Kurre Nielsen, et al. (2000) Behavioral Brain Research 107 : See 21-33); open field test (e.g. Holmes (2001) Neurosci. Biobehay. Rev. 25: 261-273); elevated plus maze test (e.g. Holmes (2001) above) and the like.

As used herein, "mood disorder" refers to the disruption of emotional mood or emotional state experienced by an individual over a wide period of time. Mood disorders include, but are not limited to, major depressive disorder (ie, unipolar disorder), mania, discomfort, bipolar disorder, mood modulation, circulatory temperament and the like. For example, see Diagnostic and Statistical Manual of Mental Disorders, Fourth Edition, (DSM IV).

As used herein, "anxiety disorder" refers to an unpleasant emotional state that includes a psychopsychological response to an unrealistic or imagined risk prediction that arises from an unrecognized intrapsychological contradiction. Physiological incidents include heart rate increases, respiratory rate changes, sweating, tremors, weakness and fatigue, and psychological incidents include imminent dangers, helplessness, concern and tension. Anxiety disorders include, but are not limited to, panic disorder, obsessive compulsive disorder, post-traumatic stress disorder, social phobia, social anxiety disorder, single phobia, generalized anxiety disorder.

As used herein, an "obsessive-compulsive disorder" or "OCD" is an anxiety disorder characterized by recurrent obsessions or acts that are significant enough to cause significant distress in an individual. These are typically time consuming and/or significantly interfere with a person's normal functionality, social activities or relationships. Obsessions are recurrent thoughts, thoughts, images or impulses that enter the heart and are persistent, intrusive and unwelcome. Often, efforts are made to ignore or suppress thoughts or to neutralize them with some other thought or action. Individuals can recognize obsession as a result of their own mind. Obsessive action is a repetitive, intentional behavior or movement that takes place in response to an obsession and typically neutralizes or prevents discomfort or some fearful event or situation Planned. For example, common obsessions involve the idea of dirt, and excessive, repetitive and unintended hand washing is a common obsession.

As used herein, "major depressive disorder", or "unipolar disorder" refers to a mood disorder that includes any of the following symptoms: Sustained, sad, anxious or "disappointed" mood; despair or pessimism; guilt, uselessness or helplessness; loss of interest or joy in previously enjoyed hobbies and activities, including sexual intercourse; reduced vitality, fatigue , “slowed down”; difficult to concentrate, remember, or determine; insomnia, early morning awakening or sleeping; appetite and/or weight loss or overeating and weight gain; death thought or suicide or suicide attempt; restlessness or irritation or persistent physical symptoms that do not respond to treatment such as headache digestive disorders and chronic pain. For example, various subtypes of depression are described in DSM IV.

As used herein, “bipolar disorder” is a mood disorder characterized by going back and forth between extreme moods. Persons with bipolar disorder usually experience a cycle of moods where attempts are very energized or frustrated (gonorrhea) to sadness and despair (depression) and then swing back to return. Diagnosis of bipolar disorder is described, for example, in DSM IV. Bipolar disorders include bipolar disorder I (mania with or without major depression) and bipolar disorder II (hypomania with major depression), see for example DSM IV.

As used herein, “pain” is a distressing feeling often caused by intense or damaging stimuli. Pain encompasses central pain syndrome, which is neuropathic pain in the central nervous system, and can occur in stroke patients or patients with multiple sclerosis, as well chronic rheumatological and musculoskeletal disorders. Pain also encompasses peripheral neuropathy which happens when the nerves that are located outside of the brain and spinal cord (peripheral nerves) are damaged. This condition often causes weakness, numbness and pain, usually in the hands and feet. It also can affect other areas and body functions including digestion and urination. Corticosteroids reduce pain by reducing inflammation and edema associated with tumors and depolarization of damaged nerves. Dexamethasone is the most commonly used corticosteroid owing to its lack of mineralocorticoid effects, long half-life, and higher potency compared with other corticosteroids. Pain includes, but is not limited to, headaches, nociceptive pain, neuropathic pain (peripheral neuropathy (diabetes, HIV, chemotherapy, radiation treatment), neuralgia (e.g trigeminal neuralgia), spinal cord compression, plexopathy), somatic pain (burn, fractures, incisions, wounds, cellulitis, shingles, arthritis, gout, musculo-skeletal pain), visceral pain (tumor invasion; obstructions (bowel, ureter, bile duct); colic; angina; pancreatitis), nociplastic pain (fibromyalgia, complex regional pain syndrome type 1, irritable bowel syndrome, bladder pain syndrome), and mixed pain (cancer pain; lower back pain; osteoarthritis pain; persistent post-surgical pain).

The International Association for the Study of Pain defines pain as “an unpleasant sensory and emotional experience associated with, or resembling that associated with, actual or potential tissue damage.” Pain is usually transitory, lasting only until the noxious stimulus is removed or the underlying damage or pathology has healed, but some painful conditions, such as rheumatoid arthritis, peripheral neuropathy, cancer and idiopathic pain, may persist for years. Pain that lasts a long time is called “chronic” or “persistent”, and pain that resolves quickly is called “acute”. Traditionally, the distinction between acute and chronic pain has relied upon an arbitrary interval of time between onset and resolution; the two most commonly used markers being 3 months and 6 months since the onset of pain.

ASIC1a Inhibition by Triol

ASIC1a channels, which form voltage-independent cation channels activated by extracellular acidification, are involved in peripheral and central (i.e., spinal cord) sensitisation in different models of inflammatory, neuropathic and visceral pain. Blocking ASIC1a affects multiple forms of synaptic plasticity in many brain regions including the amygdala and hippocampus. Inhibition of ASIC1a produces a reduction in magnitude of both forms of synaptic plasticity long-term potentiation (LTP) and long-term depression (LTD) and ASIC1a KO mice show impairment of learning and memory evaluated with the Morris water maze and elevated-plus maze behavioral tests.

This study demonstrated that the cholesterol metabolite, cholestane-3β, 5α, 6β-triol (Triol), inhibits ASICs in a subunit-dependent manner. Triol is derived from cholesterol by oxidation via formation of 5α, 6α-epoxycholesterol and 5β, 6β-epoxycholesterol as intermediates. It inhibits homomeric ASIC1a and ASIC3, and heteromeric ASIC1a/2a and ASIC1a/2b channels. The inhibition on ASIC1a is use-dependent and voltage-independent. The structure-activity analysis identifies that the hydroxy groups at the 5 and 6 positions of the A/B ring and the side chain are critical for its activity on ASIC1a-containing channels. Furthermore, this study showed that Triol protects against acidosis-induced cytotoxicity in primary cultured mouse cortical neurons and protects against ischemic brain injury through inhibition of ASIC1a.

Cholesterol is known to have significant effects on the mechanical properties of membranes, increasing their mechanical strength, affecting fluidity and surface charge of lipid membranes and thereby channel properties. These reports raise the question of whether Triol, like its metabolic precursor cholesterol, partitions into plasma membranes, alters the membrane properties, and therefore modifies the gating of ASICs nonspecifically. Regarding this, it is important to provide a comparative analysis of Triol with cholesterol, at the same micromolar concentrations. These findings show that cholesterol does not affect ASICs. In addition, none of its structure-related analogs, including cholesterol, 5α,6α-epoxycholesterol, 5β,6β-epoxycholesterol, 5α-androst-3β, 5, 6β-triol, shows a significant effect on ASIC currents. Furthermore, this data shows that Triol selectively inhibits ASIC1a and ASIC3 without affecting ASIC1β and ASIC2a. This evidence together suggests that the effect of Triol on ASICs is specific. Nevertheless, identification of the specific binding site in the future will provide direct and convincing evidence.

ASIC1β shares high sequence similarity with ASIC1a. The difference between ASIC1a and ASIC1β lies in the first 172 amino acids, including a short intracellular N-terminus, a transmembrane domain, and a short extracellular domain. Based on the data that Triol inhibits ASIC1a without affecting ASIC1β, we speculate that the amino acids that interact with Triol and mediate its inhibitory effect on ASIC1a may exist within the first 172 amino acids. Construction of the chimeric ASIC1a/1β channels, which contain different regions of the first 172 amino acids of ASIC1a, will help identify the target region. Once the target region is identified, further site-direct mutations within this region will help determine the interacting amino acids.

ASICs have been shown to play important roles in neurological diseases such as brain ischemia seizure, and pain. Pharmacological inhibition or knockout of ASIC1a offers a potent protection against ischemic brain injury. Unlike NMDA receptor antagonists, inhibition of ASIC1a provides a more prolonged therapeutic time widow of >5 h for stroke, which will vastly increase the chances for stroke intervention. Triol functions as an endogenous neuroprotectant in the spinal cord and brain ischemia, and blockade of NMDAR might be one of the underlying mechanisms. Inhibition of NMDAR, however, provides a limited time window in rodent (1-2 h), which cannot satisfactorily explain the longer therapeutic time window of at least 4 h for Triol for stroke treatment. This discrepancy suggests that additional mechanisms other than NMDA receptor inhibition might exist. This study provides strong evidence that the inhibition of ASIC serves as an important mechanism underlying its neuroprotective activity. The electrophysiology data provide direct evidence that Triol inhibits homomeric ASIC1a and heteromeric ASIC1a/2b, which are implicated in acidosis- and ischemia-induced neuronal injury. The inhibition of NMDAR by Triol may protect brain ischemia within the first 1-2 h. To separate this effect from the NMDAR blockade, the study administered Triol at 3 h after the stroke. This study found that Triol still exerts significant protection, and this protection is largely diminished by ASIC1a and ASIC1a/2b inhibitor PcTX1 or ASIC1 gene knockout, suggesting an ASIC1a-dependent mechanism. In contrast, it still shows significant protection in ASIC2 knockout mice, which predominantly express homomeric ASIC1a in the brain.

A transient increase of Triol after a sub-lethal ischemic preconditioning event, with a 4 to 5-fold maximal increase at 4 h 30 has been shown. Interestingly, the neuroprotection induced by ischemic preconditioning was blocked when a specific inhibitor of Triol synthesis suppressed the inducible increase of Triol levels. These observations suggest that Triol may function as an endogenous neuroprotectant. The 4~5-fold concentration increase corresponds to 1~1.25 μM, at which concentration Triol could inhibit ~20% ASIC1a current within 5 min, and more inhibition would be observed over longer perfusion time. Thus, the inhibition of ASIC1a by Triol might be a novel and important mechanism underlying its endogenous neuroprotective activity.

Activation of ASICs, such as ASIC1a and ASIC3, is implicated in pain sensation. Particularly, the activation of ASIC3 has been well studied in pain sensation, including chronic pain. ASIC3 can conduct biphasic currents: a rapidly desensitizing peak current and a sustained non-desensitizing current that lasts as long as the extracellular pH remains acidic. The sustained current, which persistently depolarizes the neuronal membrane, may be implicated in long-lasting pain sensation. ASIC3 inhibitor, e.g., sea anemone peptide Ugr 9-1, significantly reversed inflammatory and acid-induced pain. It has been shown that activation of ASIC1a by Texas coral snake toxin produces intense and prolonged pain, and inhibition of ASIC 1 a/2a by black mamba venom shows potent analgesic effect. The inhibitory effects of Triol on ASIC1a, ASIC1 a/2a, and ASIC3 strongly suggest that Triol might be a promising drug candidate for pain management.

In summary, this study shows that the cholesterol metabolite, cholestane-3β, 5α, 6β-triol, functions as a novel ASIC inhibitor. Inhibition of ASIC1a homomeric and heteromeric channels may be an important mechanism underlying its neuroprotective activity in ischemic stroke. Triol may represent a promising drug candidate for stroke intervention, considering the potential translation of ASIC1a inhibitor for stroke. In addition, Triol, as a small molecule ASIC1a inhibitor may provide an important pharmacological tool for the investigation of ASIC1a functions.

II. Method of Treatment of Depression

The present application provides a method for treating depression with Triol (and, in certain embodiments, related compounds). One of ordinary skill will understand that cholestane-3β, 5α, 6β-triol (Triol) as described herein has a specific chemical structure. However, in certain embodiments, generic substitutions of elements within the chemical structure of Triol or analog compounds may be used in the methods herein.

The chemical structures of Triol and some related compounds are shown below:

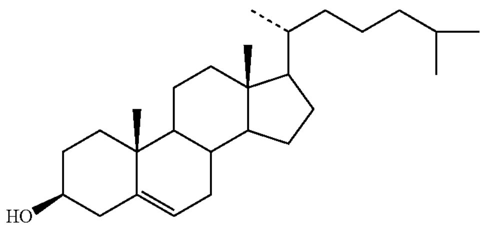

Cholesterol

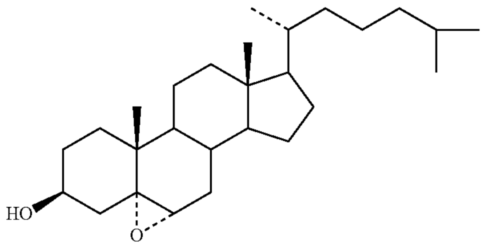

5α,6α-epoxycholesterol

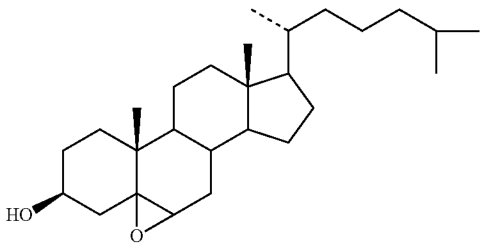

5β,6β-epoxycholesterol

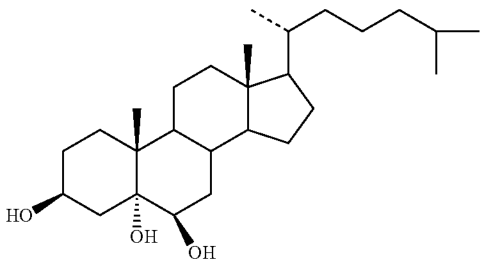

cholestane-3β, 5α, 6β-triol (Triol)

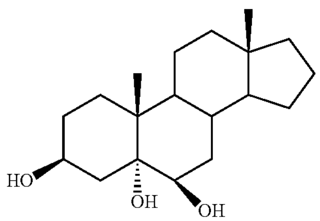

5α-androst-3β, 5, 6β-triol

-continued
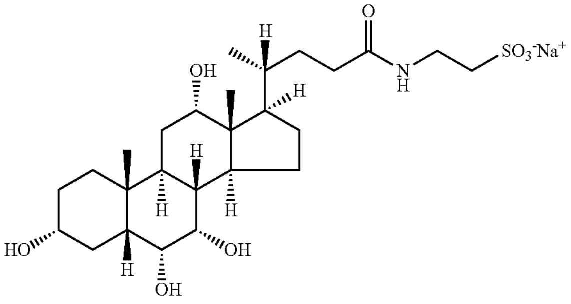
Tauro-3a, 6a, 7a, 12a-tetrahydroxy bile acid
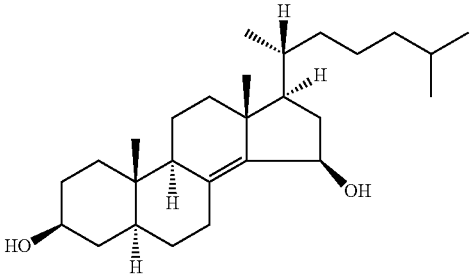
15β-hydroxycholestene
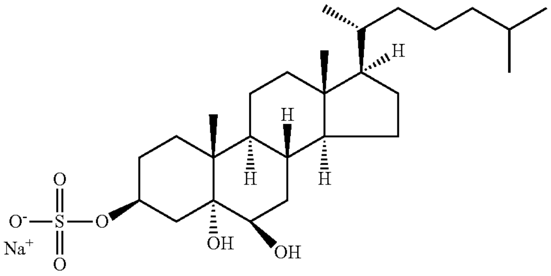
cholestane-3-sulfate-5a, 6β-Diol
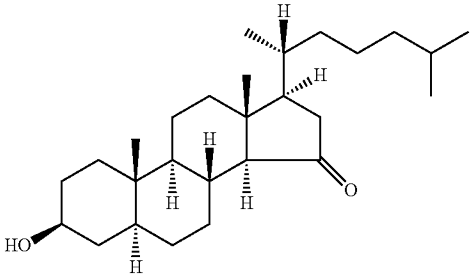
15-ketocholestane
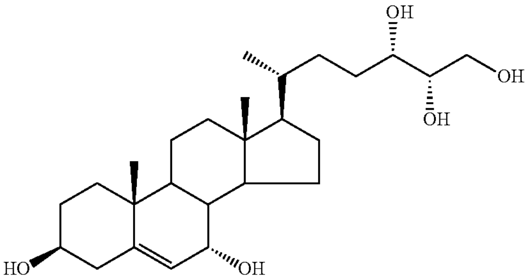
7a, 24S, 27-trihydroxycholesterol
-continued
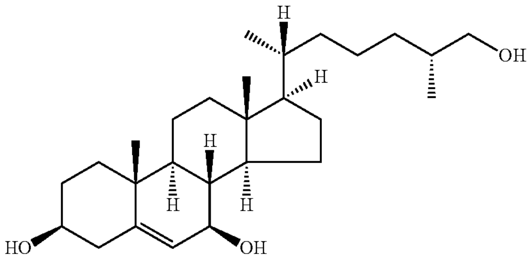
7β, 27-dihydroxycholesterol
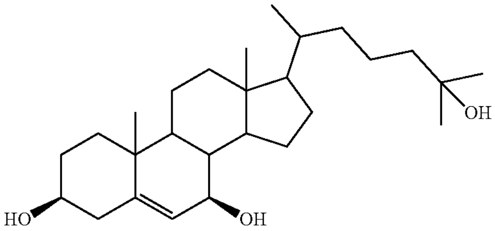
7β, 25-dihydroxycholesterol
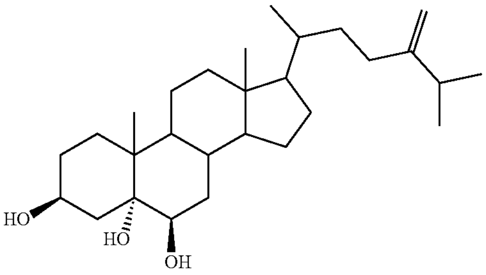
24-methylenecholestane-3β, 5a, 6β-triol
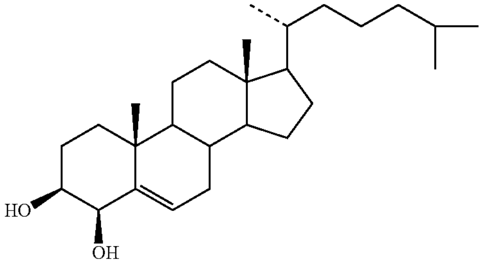
4β-hydroxy Cholesterol
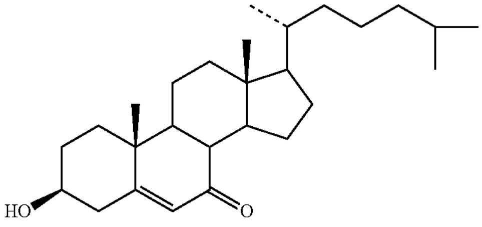
7-keto Cholesterol
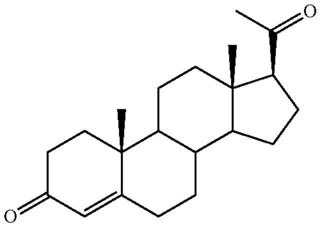
Progesterone -continued
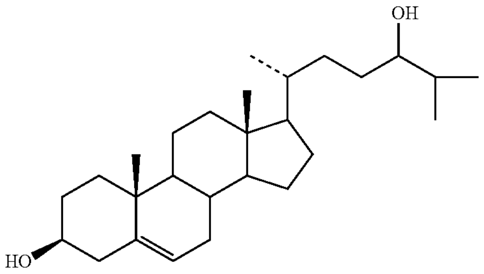
24(S)-hydroxy Cholesterol
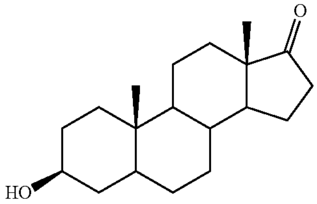
Ancrosterone
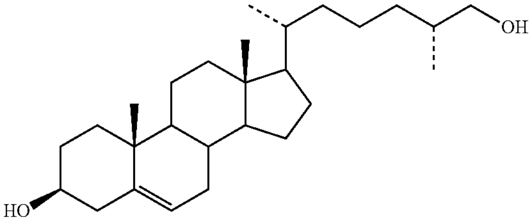
27-hydroxy Cholesterol
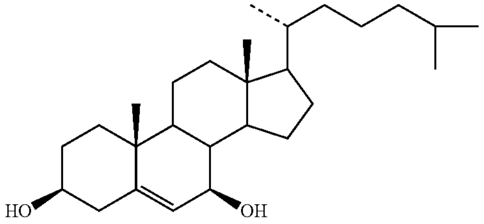
7β-hydroxy Cholesterol
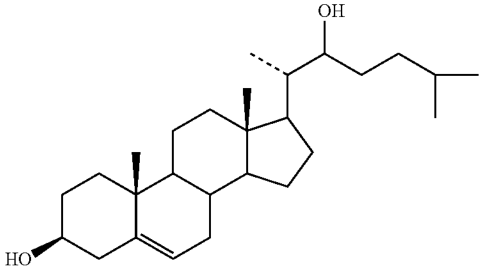
22(R)-Hydroxycholesterol
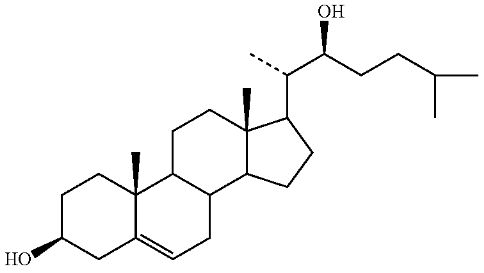
22(S)-Hydroxycholesterol
-continued
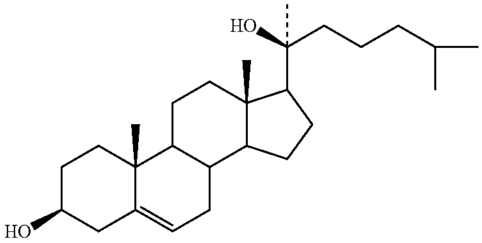
20a-Hydroxycholesterol
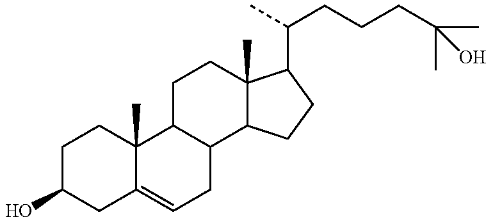
25-Hydroxycholesterol
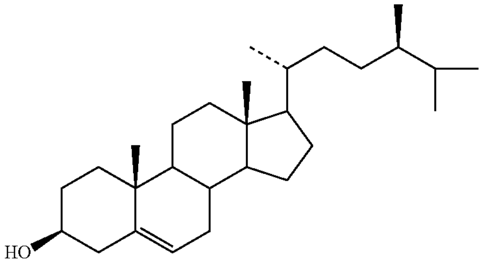
24a-methyl Cholesterol
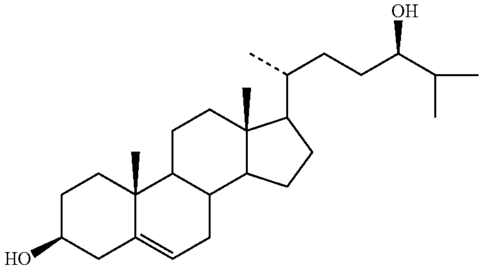
24(R)-hydroxy Cholesterol
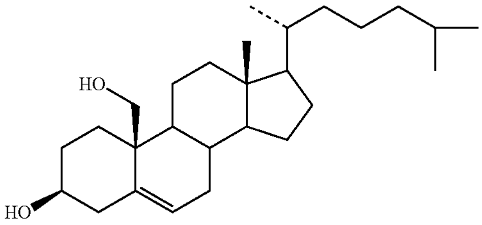
19-hydroxy Cholesterol
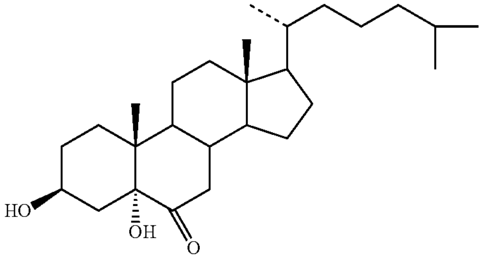
5a-hydroxy-6-keto Cholesterol -continued

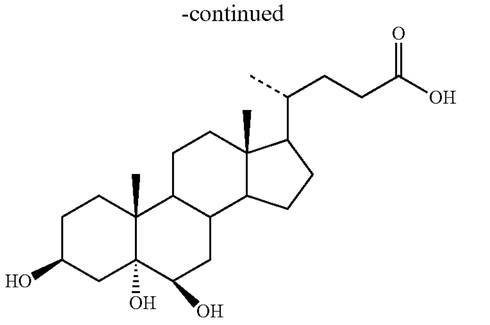

3β, 5a, 6β-Trihydroxycholanoic Acid

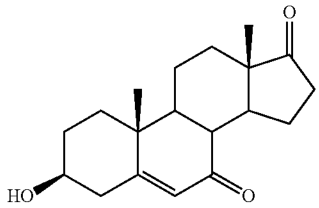

7-keto Dehydroepiandrosterone

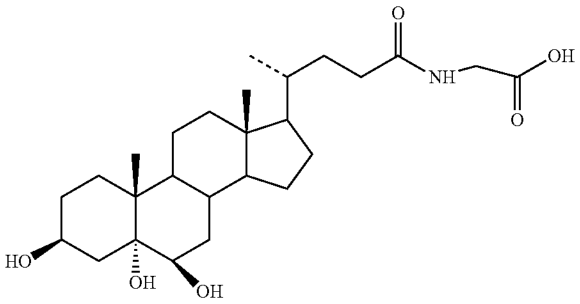

Glyco-3β, 5a, 6β-Trihydroxycholanoic Acid

Treatment with Triol in a patient having depression can decrease levels of depression symptoms, including, but not limited to, physical discomfort, depression, loss of pleasure, suicide propensity, agitation, anxiety, drug withdrawal symptoms and the like.

An aspect of the application is a method of treating depression, comprising: administering a subject in need a therapeutically effective amount of a composition comprises triol.

In certain embodiments, the triol is administered to said subject to reduce depression resulting from a trauma. In certain embodiments, the triol is administered to said subject nasally, intrathecally, and/or epidurally. In certain embodiments, the step of administering is performed at least about two hours after the onset of trauma on the subject. In certain embodiments, the triol is administered to said subject following a trauma.

Another aspect of the application is a method of treating headaches, comprising: administering a subject in need a therapeutically effective amount of a composition comprises triol.

In certain embodiments, the triol is administered to said subject to reduce headaches resulting from a migraine. In certain embodiments, the triol is administered to said subject nasally, intrathecally, and/or epidurally. In certain embodiments, the step of administering is performed at least about two hours after the onset of migraine on the subject. In certain embodiments, the triol is administered to said subject following a migraine.

An aspect of the application is a method of treating depression in a patient comprising administering to a patient in need thereof a therapeutically effective amount of a pharmaceutical composition comprising triol, and a pharmaceutically acceptable carrier.

An aspect of the application is a method of preventing depression in a patient comprising administering to a patient in need thereof a therapeutically effective amount of a pharmaceutical composition comprising triol, and a pharmaceutically acceptable carrier.

In certain embodiments, the depression is a unipolar disorder. In certain embodiments, the triol is packaged for delivery in a titratable dosage form. In certain embodiments, the triol is packaged such that delivery is targeted to an area selected from the group consisting of: sublingual; buccal; parenteral; oral; rectal, nasal; and the pulmonary system. In certain embodiments, the triol is in the form selected from the group consisting of: gel; gel spray; tablet; liquid; capsule and for vaporisation. In certain embodiments, the triol is formulated as a ratioed product from: a) a pharmaceutical composition which comprises triol; and b) an anti-depressant agent. In certain embodiments, the method further comprising administering to the patient in need thereof a therapeutically effective amount of one or more other medicinal substances. In certain embodiments, the one or more other medicinal substances are one or more anti-depressant drugs. In certain embodiments, the one or more other medicinal substances are one or more pain relief related drugs.

Symptoms of depression in non-human animal models include, for example, a decrease in escape-related behavior. A given test agent (e.g., a test agent that is a candidate agent for treating depression) increases escape-related behavior compared to control animals that are not treated with the test agent. For example, in some cases, a given test agent (e.g., a test agent that is a candidate agent for treating depression) is at least about 10%, at least about at least compared to a control animal that is not treated with the test agent. Increase escape-related behavior by 20%, at least about 30%, at least about 40%, at least about 50%, at least about 2-fold or more.

In some embodiments, the test agent increases performance in the tail suspension test. The tail suspension test is based on the fact that animals subjected to short-term inevitable stresses suspended by these tails will develop an immobile posture. Compared to control animals that are not treated with a test drug, a test drug that is a candidate drug for treating depression will reduce immobility and promote the development of escape-related behaviors.

In the context of a depressive phenotype, motivation is assayed by presenting inevitable stressors to the rodent, such as suspension by the tail of the animal or forced swimming in cold water. Assay analysis requires quantifying the ratio of the time an animal spends doing escape-related behavior or struggling compared to the time spent resting. Immobility in such assays, suspension in tail suspension test (TST), or suspension in forced swim test (FST) has been historically interpreted as a sign of "behavioral despair."

The methods of administration, dosage and formulation described herein may all be used with the methods of treatment of depression described herein.

III. Method of Treatment of Pain

An aspect of the application is a method of treating pain, comprising: administering a subject in need a therapeutically effective amount of a composition comprises triol.

In certain embodiments, the pain was caused by acidosis. In certain embodiments, the pain was caused by stroke. In certain embodiments, the triol is administered to the subject nasally, intrathecally, and/or epidurally.

An aspect of the application is a method of treating pain in a patient comprising administering to a patient in need thereof a therapeutically effective amount of a pharmaceutical composition comprising triol, and a pharmaceutically acceptable carrier.

In certain embodiments, the pain is allodynia. In certain embodiments, the triol is packaged for delivery in a titratable dosage form. In certain embodiments, the triol is packaged such that delivery is targeted to an area selected from the group consisting of: sublingual; buccal; parenteral; oral; rectal, nasal; and the pulmonary system. In certain embodiments, the triol is in the form selected from the group consisting of: gel; gel spray; tablet; liquid; capsule and for vaporisation. In certain embodiments, the triol is formulated as a ratioed product from: a) a pharmaceutical composition which comprises triol; and b) an anti-depressant agent. In certain embodiments, the method further comprising administering to the patient in need thereof a therapeutically effective amount of one or more other medicinal substances. In certain embodiments, the one or more other medicinal substances are one or more anti-depressant drugs. In certain embodiments, the one or more other medicinal substances are one or more pain relief related drugs.

An aspect of the application is a method of preventing pain in a patient comprising administering to a patient in need thereof a therapeutically effective amount of a pharmaceutical composition comprising triol, and a pharmaceutically acceptable carrier.

Thermal hypersensitivity in pain and sham animals is assessed using ankle/paw-immersion test in water maintained at 46.0±0.2 °C using a thermoregulated water bath. The ankle/paw of rat is immersed in water until the paw is withdrawn. The duration of ankle/paw immersion is recorded, and a cut-off time of 25 s is used to avoid any tissue damage. Rats have been habituated to the testing procedures and to handling by the investigator during the week prior to the experiment. Treatments have been administered after measurement of two consecutive stable withdrawal threshold values that differ by not more than 10%, with at least a 10 min interval between two measurements. Paw withdrawal threshold are assessed at baseline pre- and post-CFA, 15 and 45 min following Triol or saline administration.

Rodent hindpaw inflammation is a commonly used model of persistent inflammatory pain in which noxious stimuli are applied to the glabrous (thermal) or glabrous and hairy (mechanical) skin of the hindpaw. Response measures are typically hindpaw withdrawal latency to heat (seconds) or mechanical withdrawal threshold (g or mN). Once baseline response measures have been determined, an inflammogen is injected into either the dorsal hairy or ventral glabrous skin and withdrawal responses are assessed over time (hours to days). Post-treatment response measures are hyperalgesic, meaning that response latency to heat is faster and mechanical withdrawal thresholds (typically assessed using von Frey-like nylon monofilaments, each of which has a different bending force) are lower. Edema, which is also a consequence of such an injection, is greatest after the injection of carrageenan (or carrageenan plus kaolin) and least following complete Freund's adjuvant (CFA).

Models of persistent muscle pain include intramuscular injection of carrageenan or acidic saline. Unilateral injection of carrageenan into the gastrocnemius muscle of rats produces acute inflammation with edema and reduced withdrawal latencies in the first 4 to 24 hours. Hyperalgesia also develops in the contralateral limb 1 to 2 weeks after injection, suggesting involvement of central nervous system mechanisms. Mechanical and thermal hyperalgesia are dependent on the concentration of carrageenan and may last 7 to 8 weeks.

IV. Administration

The antagonist (e.g., Triol) may be administered to the subject with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, the antagonist is administered directly to a tumor or cancer tissue, including administration directly to the tumor bed during invasive procedures. The antagonist may also be placed on a solid support such as a sponge or gauze for administration against the target chemokine to the affected tissues.

Antagonists can be administered in the usually accepted pharmaceutically acceptable carriers. Acceptable carriers include, but are not limited to, saline, buffered saline, glucose in saline. Solid supports, liposomes, nanoparticles, microparticles, nanospheres or microspheres may also be used as carriers for administration of the antagonists.

One or more of the biomarker agonists or antagonists discussed herein may be administered in combination with other pharmaceutical agents, as well as in combination with each other. The term "pharmaceutical" agent as used herein refers to a chemical compound which results in a pharmacological effect in a patient. A "pharmaceutical" agent can include any biological agent, chemical agent, or applied technology which results in a pharmacological effect in the subject.

The therapeutic compositions administered by these methods are administered directly into the environment of the targeted cell undergoing unwanted proliferation, e.g., a cancer cell or targeted cell (tumor) microenvironment of the patient. Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. Routes of administration may be combined, if desired. In some embodiments, the administration is repeated periodically.

The therapeutic agents of the present application, i.e., antagonists or other selected antagonists, may be administered to a patient, preferably suspended in a biologically compatible solution or pharmaceutically acceptable delivery vehicle. The various components of the compositions are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

Because the compositions do not have to cross the blood-brain-barrier, alternate compositions can be provided which do not meet the characteristics required to do so, yet still inhibit the action of a given biomarker target. Thus, in yet another aspect, a method of screening molecules for use in cancer therapy comprises contacting a mammalian cancer or tumor cell culture which expresses a biomarker of the present application, such as GABRA3 or other selected targets with a potential therapeutic molecule, e.g., a small molecule, peptide, polynucleotide, antibody, or the like; and culturing the cell. The culture is then tested for inhibition of cellular migration. Cellular migration assays are known to one of skill in the art. Other methods are known in the art. If cellular migration is decreased as compared to a control, the molecule has an anti-tumor or anti-cancer effect or prevents or reduces cancer metastasis. The level of cellular migration in the test cell culture can be compared to the level of cellular migration in untreated cancer/tumor cell cultures.

V. Dosage

The appropriate dosage ("therapeutically effective amount") of the antagonist (e.g., Triol) will depend, for example, on the condition to be treated, the severity and course of the condition, whether the antagonist is administered for preventive or therapeutic purposes, previous therapy, the patient's clinical history and response to the agonist or antagonist, the type of agonist or antagonist used, and the discretion of the attending physician. The antagonist is suitably administered to the patient at one time or over a series of treatments and may be administered to the patient at any time from diagnosis onwards. The agonist or antagonist may be administered as the sole treatment or in conjunction with other drugs or therapies useful in treating the condition in question.

As a general proposition, a therapeutically effective amount of antagonist(s) will be administered individually or collectively in the range of about 1 ng/kg body weight/day to about 100 mg/kg body weight/day whether by one or more administrations. In a particular embodiments, the range of antibody administered is from about 1 ng/kg body weight/day to about 1 μg/kg body weight/day, 1 ng/kg body weight/day to about 100 ng/kg body weight/day, 1 ng/kg body weight/day to about 10 ng/kg body weight/day, 10 ng/kg body weight/day to about 1 μg/kg body weight/day, 10 ng/kg body weight/day to about 100 ng/kg body weight/day, 100 ng/kg body weight/day to about 1 μg/kg body weight/day, 100 ng/kg body weight/day to about 10 μg/kg body weight/day, 1 μg/kg body weight/day to about 10 μg/kg body weight/day, 1 μg/kg body weight/day to about 100 μg/kg body weight/day, 10 μg/kg body weight/day to about 100 μg/kg body weight/day, 10 μg/kg body weight/day to about 1 mg/kg body weight/day, 100 μg/kg body weight/day to about 10 mg/kg body weight/day, 1 mg/kg body weight/day to about 100 mg/kg body weight/day and 10 mg/kg body weight/day to about 100 mg/kg body weight/day.

In another embodiment, the biomarker agonist(s) or antagonist(s) are administered individually or collectively at a dosage range of 1 ng-10 ng per injection, 10 ng to 100 ng per injection, 100 ng to μg per injection, 1 μg to 10 μg per injection, 10 μg to 100 μg per injection, 100 μg to 1 mg per injection, 1 mg to 10 mg per injection, 10 mg to 100 mg per injection, and 100 mg to 1000 mg per injection. The antagonist may be injected daily, or every 2, 3, 4, 5, 6 and 7 days, or every 1, 2, 3 or 4 weeks.

In another particular embodiment, the dose range of the antagonist(s) may range from about 1 ng/kg to about 100 mg/kg In still another particular embodiment, the range of antagonist, such as an antibody administered is from about 1 ng/kg to about 10 ng/kg, about 10 ng/kg to about 100 ng/kg, about 100 ng/kg to about 1 μg/kg, about 1 μg/kg to about 10 μg/kg, about 10 μg/kg to about 100 μg/kg, about 100 μg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the antagonist(s) is administered individually or collectively in an amount of about, 0.0006, 0.001, 0.003, 0.006, 0.01, 0.03, 0.06, 0.1, 0.3, 0.6, 1, 3, 6, 10, 30, 60, 100, 300, 600 and 1000 mg/day. As expected, the dosage will be dependent on the condition, size, age, and condition of the patient.

The antagonist(s) may be administered, as appropriate or indicated, a single dose as a bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

The dosages and treatment regimens utilizing the biomarker agonist(s) or antagonist(s) of the present application can be determined by the person of skill in the art. Certain of the GABRA3 antagonists are approved for use for the treatment of other conditions, and thus dosages and prescribing information is known. For example, in the case of flumazenil, in one embodiment, a dosage of from about 10 nM to about 10 μM is provided to treat multiple myeloma. In another embodiment, a dosage of 0.4 mg-1.0 mg IV is provided.

The dosage required for the biomarker agonist(s) or antagonist(s) depends primarily on factors such as the condition being treated, the age, weight, and health of the patient, and may thus vary among patients. The effective dosage of each active component is generally individually determined, although the dosages of each compound can be the same. In one embodiment, the small molecule dosage is about 1 μg to about 1000 mg. In one embodiment, the effective amount is about 0.1 to about 50 mg/kg of body weight including any intervening amount. In another embodiment, the effective amount is about 0.5 to about 40 mg/kg. In a further embodiment, the effective amount is about 0.7 to about 30 mg/kg. In still another embodiment, the effective amount is about 1 to about 20 mg/kg. In yet a further embodiment, the effective amount is about 0.001 mg/kg to 1000 mg/kg body weight. In another embodiment, the effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 μg/kg, about 75 μg/kg, about 50 μg/kg, about 25 μg/kg, about 10 μg/kg, or about 1 μg/kg. However, the effective amount of the biomarker agonist(s) or antagonist(s), as well as dosages different than that used for e.g., brain-related conditions, can be determined by the attending physician, and depends on the condition treated, the compound administered, the route of delivery, age, weight, severity of the patient's symptoms and response pattern of the patient.

Toxicity and therapeutic efficacy of the compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays (such as those described in the examples below) and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present application, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

VI. Formulations

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the application is formulated to be compatible with its intended route of administration. Examples of routes of administration include parenteral, e.g., intrathecal, intra-arterial, intravenous, intradermal, subcutaneous, oral, transdermal (topical) and transmucosal administration. In certain embodiments, the pharmaceutical composition is administered directly into a tumor tissue.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially, for example, from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the application is dictated by and directly dependent on the unique characteristics of the active compound and the particular therapeutic effect to be achieved, and the limitations inherent in the art of compounding such an active compound for the treatment of individuals.

The present application is further illustrated by the following examples that should not be construed as limiting. The contents of all references, patents, and published patent applications cited throughout this application, as well as the Figures and Tables, are incorporated herein by reference.

Example 1: Triol is an ASIC1a Inhibitor

Methods

ASICs Transfection in CHO Cells

Chinese hamster ovary (CHO) cells were cultured in F12-K medium (Invitrogen) plus 10% fetal bovine serum, 50 units/nal penicillin, and 50 μg/m1 streptomycin. At ~50% confluence, CHO cells were co-transfected with cDNAs for rat ASIC1β, ASIC2a, or ASIC3, and that for GFP. GFP-positive cells were used for electrophysiological recordings 24-72 h after transient transfection. CHO cells with stable expression of ASIC1a (CHO-ASIC1a) were utilized for the recording of ASIC1a currents {Xiong, 2004 #268}.

Primary Culture of Mouse Cortical Neurons

Mouse cortical neurons were cultured. Pregnant Swiss mice were purchased from Charles River. The use of mice for neuronal cultures was approved by the Institutional Animal Care and Use Committee of Morehouse School of Medicine. Briefly, the brains of fetuses (embryonic day 16) were removed quickly from anesthetized pregnant mice and placed in cold Ca2+/Mg2+-free PBS. Cerebral cortices were dissected and incubated with 0.05% trypsin-EDTA for 10 min at 37 °C, followed by trituration. Cells were plated in poly-L-ornithine-coated culture dishes. Cells were initially cultured in minimal essential medium (MEM) with 10% fetal bovine serum (FBS), 10% horse serum, and 25 mM glucose and maintained at 37 °C in a humidified 5% CO2 atmosphere incubator for 24 h. After that, the culture medium was completely replaced by Neurobasal medium supplemented with B-27 (Invitrogen) and then changed twice a week. Neurons were used for the experiments between days 10 and 14.

Electrophysiology

ASIC currents were recorded using patch-clamp techniques. Pipette solution contained (mM): 140 CsF, 1 CaCl2, 2 MgCl2, 11 EGTA, 2 tetraethylammonium chloride, 10 HEPES and 4 MgATP, pH 7.3 adjusted with CsOH, 290-300 mOsm. Extracellular Fluid (ECF) contained (mM): 140 NaCl, 5.4 KCl, 2 CaCl2, 1 MgCl2, 10 glucose, and 10 HEPES (320-330 mOsm). A multi-barrel perfusion system (SF-77 Warner Instruments, Hamden, CT) was used to obtain a rapid exchange of ECFs. Currents were recorded with Axopatch 200B amplifier, filtered at 2 kHz, and digitized at 5 kHz using Digidata 1332A. ASIC currents were induced by rapid perfusion of the cells with acidic ECF for 4 seconds. Unless otherwise stated, cells were clamped at a holding potential of −60 mV. Pipettes had a resistance of 3-5 MΩ when filled with the pipette solution. Data were excluded for statistical analysis when access resistance was >10 MΩ or leak current was >100 pA.

Fluorescein Diacetate/Propidium Iodide (FDA/PI) Staining

After different treatments, cells were incubated with a normal medium containing fluorescein diacetate (FDA, 5 mg/ml) and propidium iodide (PI, 2 mg/ml) for 5 min. Live (FDA-positive) and dead (PI-positive) cells were observed and counted with a fluorescent microscope (Nikon Eclipse Ti-S, Nikon) at excitation/emission wavelengths of 493/636 nm for PI and 470/535 nm for FDA.

Lactate Dehydrogenase (LDH) Assay

Cytotoxicity was measured by LDH assay using a cytotoxicity detection kit (Cat. No. 11644793001, Roche Diagnostics) according to the manufacturer's instructions. At the indicated time points, 50 μl culture medium was transferred from each well into a 96-well plate to measure LDH release. To obtain the maximal releasable LDH, cells were incubated with Triton X-100 (final concentration 0.5%) at the end of experiments for 30 min at room temperature. 50 μl mixed assay reagent from a cytotoxicity detection kit was added to each well and mixed in the dark for 30 min. The absorbance at 492 nm was measured by a spectrometer (SpectraMax Plus, Molecular Devices, Sunnyvale, CA, USA), and the reference wavelength at 620 nm was subtracted to yield the values of LDH release.

Ischemic Stroke Models

Wild-type, ASIC1a, and ASIC2a knockout mice were randomly assigned to different treatment groups. The surgeon who performed the MCAO surgery was blinded to the treatments. The experimental procedure for using mice in surgery was approved by the Institutional Animal Care and Use Committee of Morehouse School of Medicine. Transient (45 min) focal ischemia was induced by suture occlusion of the middle cerebral artery (MCAO). Mice were anesthetized using a mixture of 1.5% isoflurane, 70% N2O, and 28.5% O2. Transcranial LASER doppler was used to monitor the change in cerebral blood flow. Only the mice with a blood flow drop below 20% of the basal value were used for data analysis. 24 hours after the start of ischemia, mice were euthanized, and the brains were dissected. Coronal sections at 1 mm intervals were prepared and stained with 2% vital dye 2,3,5-triphenyltetrazolium hydrochloride (TTC). Infarct volume was calculated by summing the infarcted areas (pale) of all sections and multiplying by the thickness of the sections. The intracerebroventricular injection was performed.

Chemicals

Cholestane-3β,5α,6β-triol (Triol) and analogs including cholesterol, 5α,6α-epoxycholesterol (5α,6α-epoxy-Chol) and 5β,6β-epoxycholesterol (5β,6β-epoxy-Chol) were purchased from Cayman Chemical and Sigma Aldrich. 5α-androst-3β,5,6β-triol (Andro-triol) was synthesized, with high purity of 99.51% 35. Triol was dissolved in 20% hydroxypropyl-β-cyclodextrin (HP-β-CD), cholesterol was dissolved in acetone, and 5α,6α-epoxy-Chol, and 5β,6β-epoxy-Chol were dissolved in ethanol to make stock solutions of 10 mM.

Statistical Analysis

All data were expressed as mean±SEM. GraphPad Prism was used for statistical analysis. ANOVA followed by Bonferroni post tests were used to examine the statistical significance. The criterion for significance was set at $p<0.05$.

Results

Subunit-Dependent Inhibition of ASICs by Triol in CHO Cells

Gene knockout or pharmacological inhibition of ASIC1a provides potent neuroprotection in ischemic stroke. To determine whether inhibition of ASIC1a is an underlying mechanism for the neuroprotective activity of Triol, the study examined the effect of Triol on ASIC1a channels. The CHO cells with stable expression of homomeric ASIC1a channels (CHO-ASIC1a) were used. ASIC1a currents were induced by a pH drop from 7.4 to 6.0. Considering the run-down of ASIC1a currents, the formal recording was not started until at least three consecutive stable currents were obtained. As shown in FIG. 1A, Triol time- and concentration-dependently inhibits ASIC1a currents. The currents were inhibited by ~20 and 40% by 1 and 10 μM Triol respectively within 5 minutes of application (n=5, *$p<0.05$ and $p<0.01$ compared with vehicle; #$p<0.05$ and ##$p<0.01$ compared with 1 μM treatment) (FIG. 1B). This inhibition is irreversible, even after 30 min washout (data not shown). In contrast, application of the vehicle (0.02% HP-β-CD) shows no significant effect on ASIC1a currents (FIG. 1**A-B).

To further determine the selectivity of Triol over other ASIC subunits, the study examined the effect of Triol on homomeric ASIC1β, ASIC2a, and ASIC3 channels. ASIC1β has a high sensitivity to acidic pH drop (pH0.5 act ~6.0 for ASIC1β), whereas ASIC2a has a relatively lower sensitivity to acidic pH (pH0.5 act ~4.5) 36,37. Therefore, the study used pH 6.0 and 4.5 to activate ASIC1β and ASIC2a currents, respectively. Triol exerted no significant effect on ASIC1β and ASIC2a currents (FIG. 1C-D) (n=4 and 5). ASIC3 has biphasic currents, including the peak and sustained current components 4, which have different sensitivities to pH drop. The sustained current component has a lower sensitivity to pH drop, which could only be induced when a more acidic pH solution <6.0 is applied 32. The study used a lower pH of 5.5 to induce biphasic ASIC3 currents to examine whether Triol affects both current components. As shown in FIG. 1E-F, Triol (10 μM) significantly inhibits the ASIC3 currents. It inhibits the peak and sustained current components by ~23% and 54%, respectively, after 5 5 min application (n=4-5, **$p<0.01$ compared with the vehicle).

Triol Inhibits ASIC Currents in Primary Cultured Mouse Cortical Neurons

Figure 2:
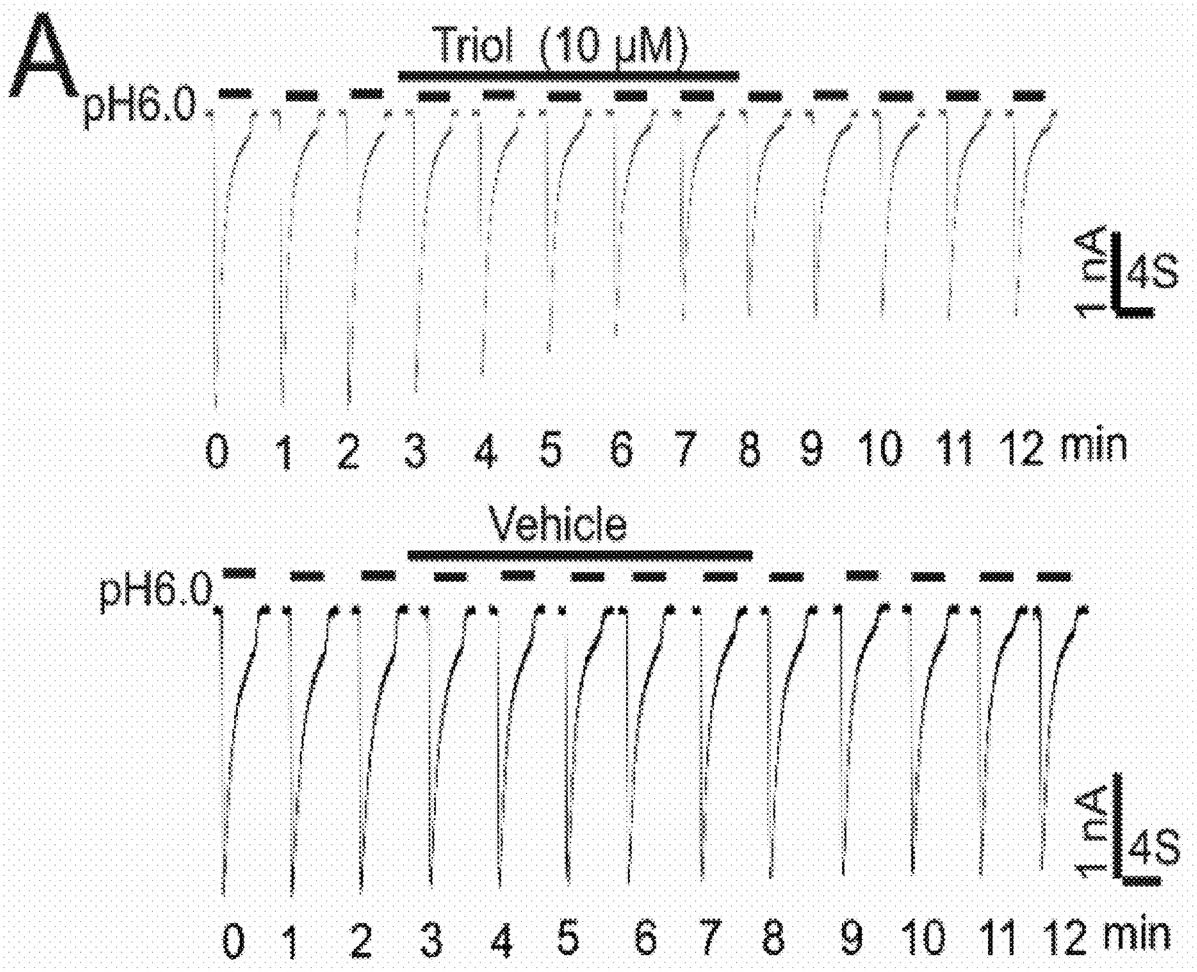
FIG. 2 shows the effect of Triol and analogs on ASIC1a-like currents in primary cultured mouse cortical neurons. (A-B) Representative current traces and summary data showing the change of ASIC1a-like currents over time in the presence of Triol (10 μM) or vehicle (n=5, *p<0.05, **p<0.01 compared with vehicle, two-way ANOVA). (C) The structure of Triol and its precursors or analogs including cholesterol, 5α,6α-epoxycholesterol (5α,6α-epoxy-Chol), 5β,6β-epoxycholesterol (5β,6β-epoxy-Chol) and 5α-androst-3β, 5, 6β-triol (Andro-triol). (D-F) Representative current traces and summary data showing the change of ASIC currents over time in the presence of 10 μM cholesterol, 5α,6α-epoxy-Chol, 5β,6β-epoxy-Chol and Andro-triol (n=3, two-way ANOVA).
Figure 2:
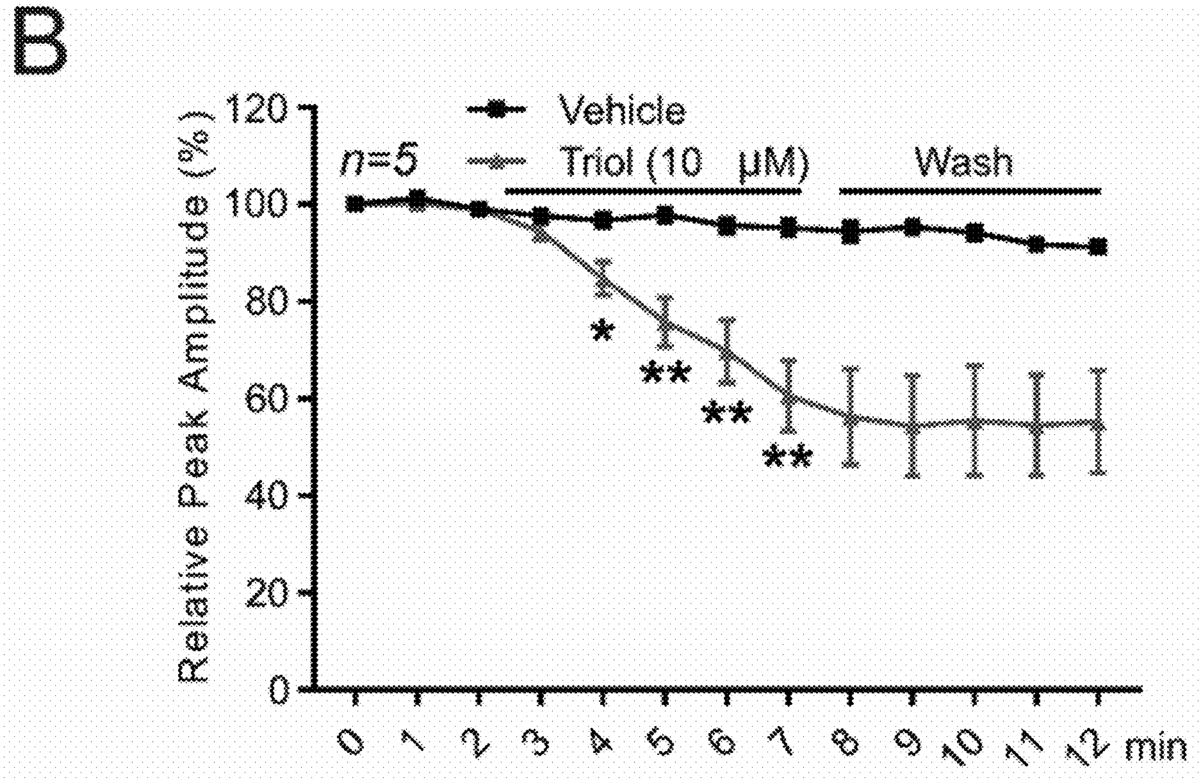
Figure 2:
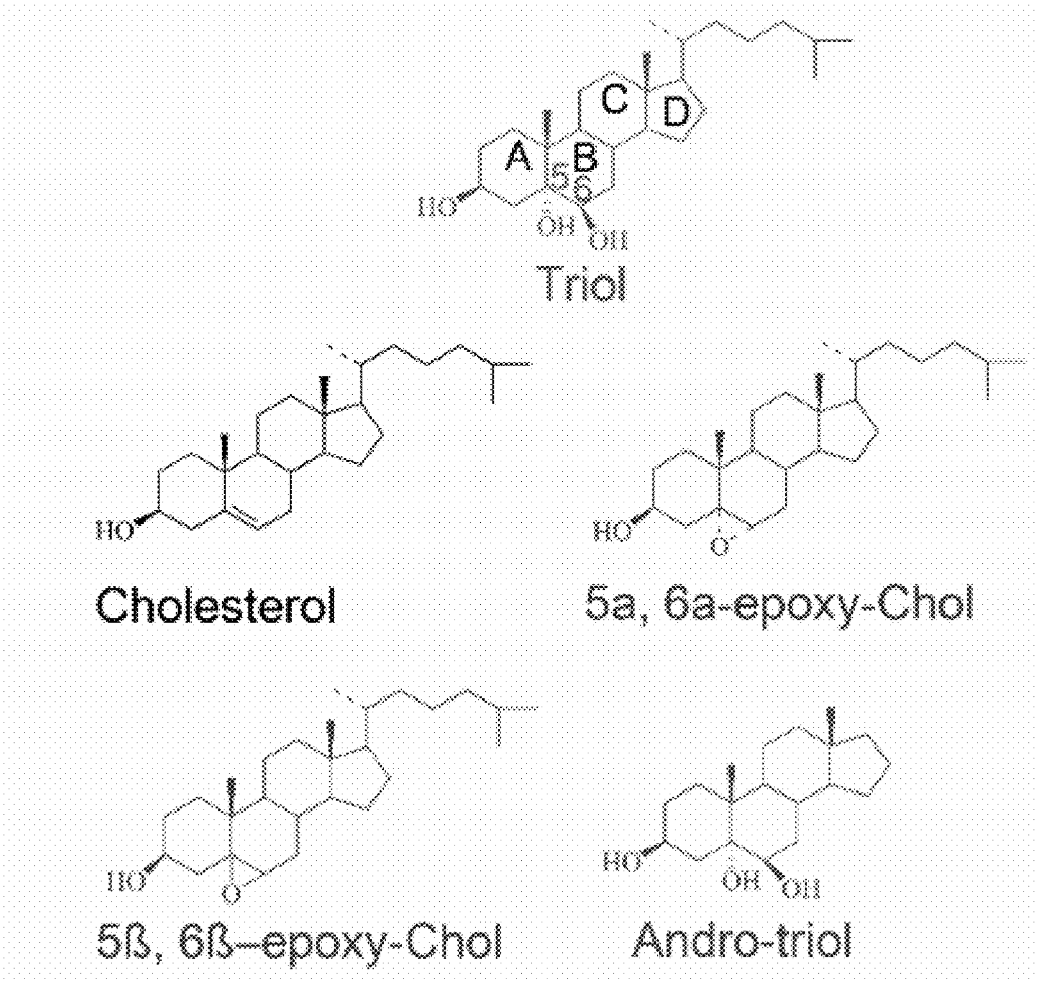
Figure 2:
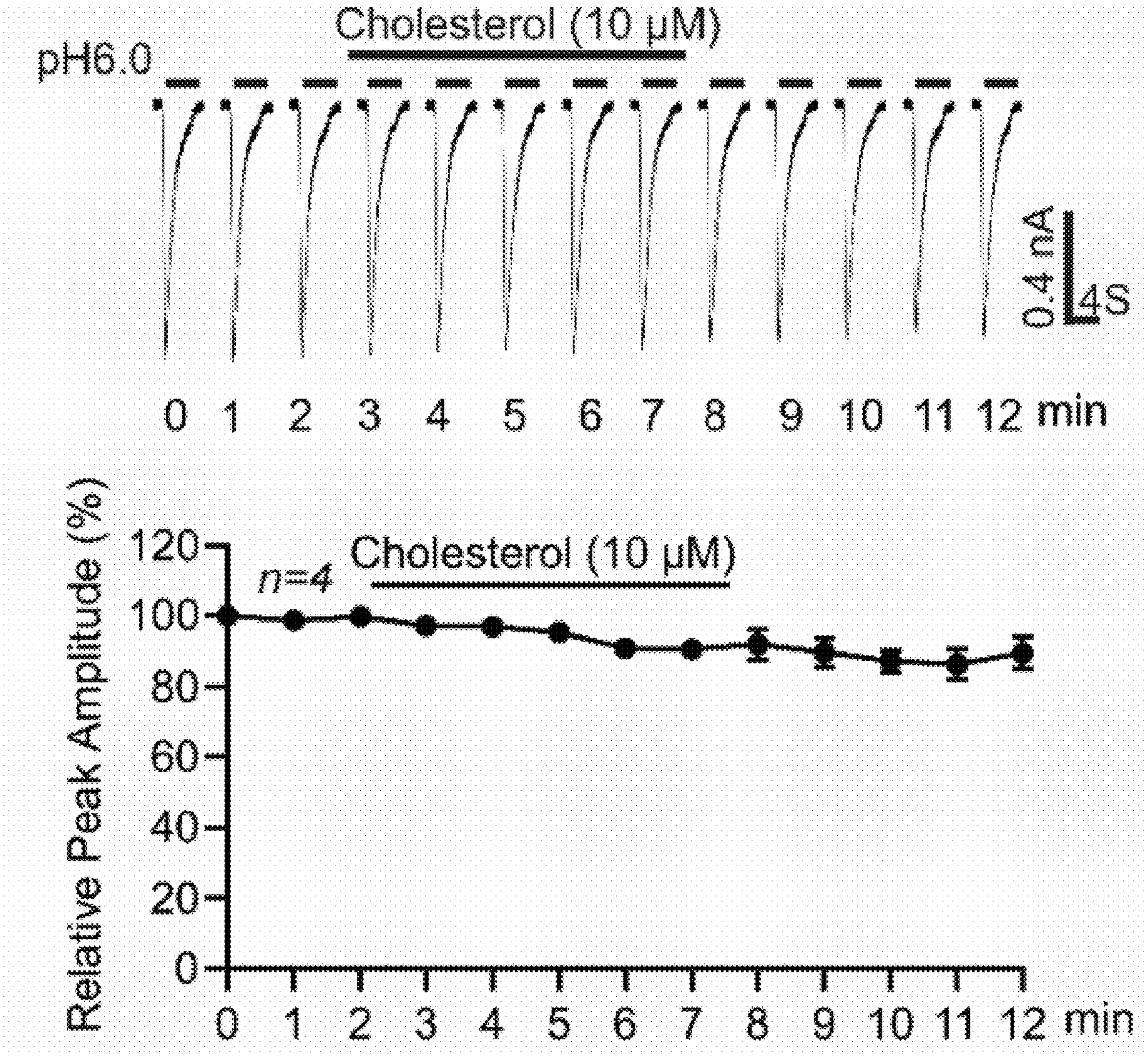
Figure 2:
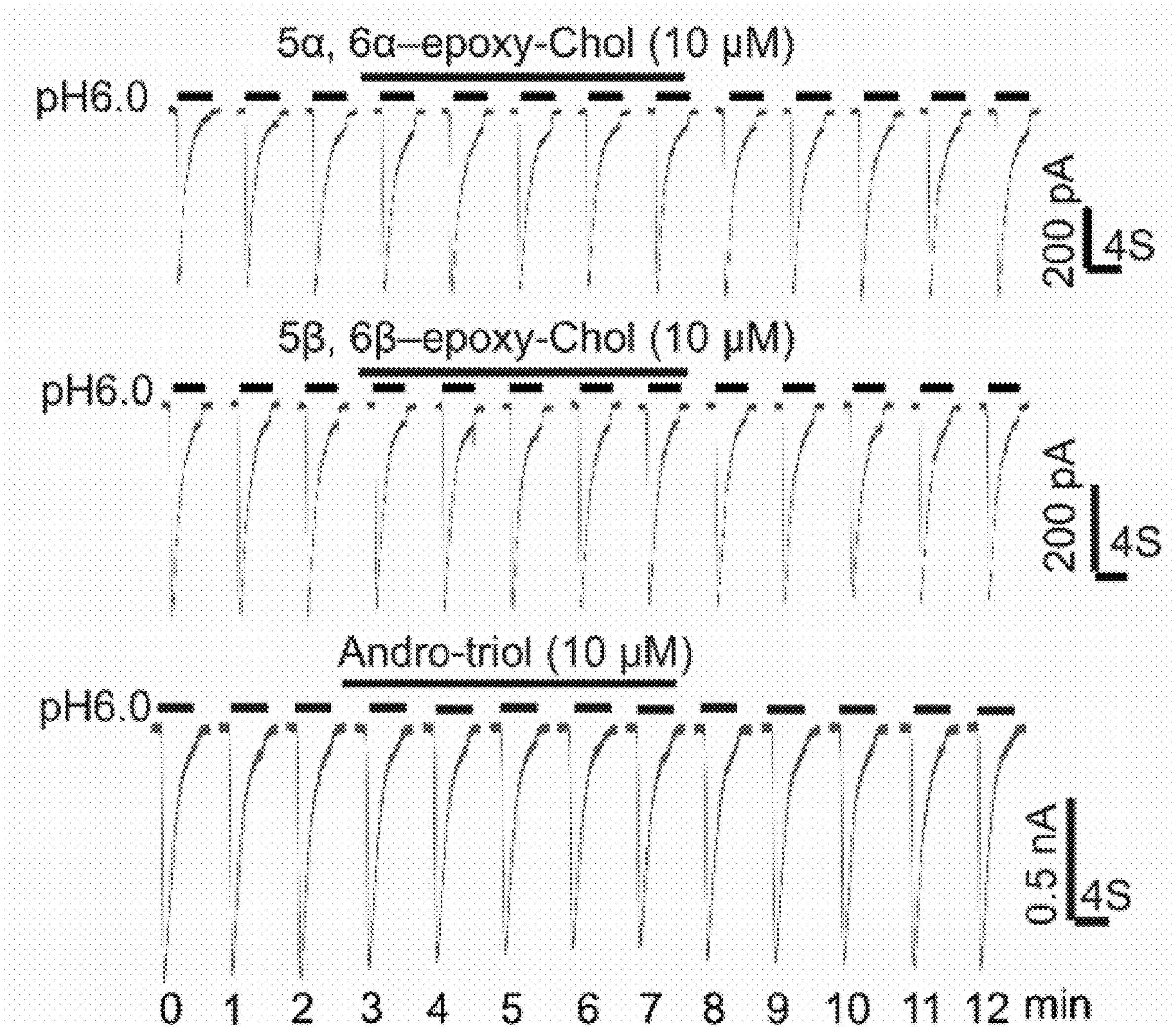
Figure 2:
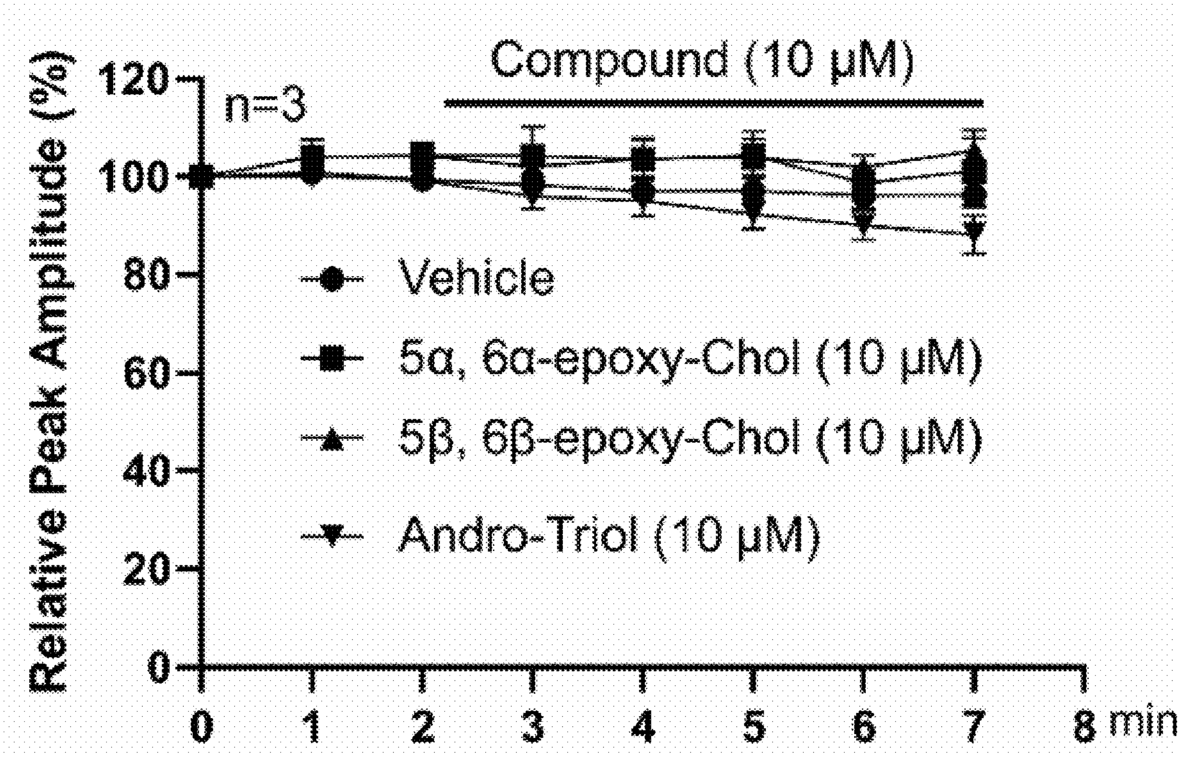

ASIC1a is the predominant ASIC subunit expressed in the central neurons, and ASIC currents in central neurons are mainly mediated by ASIC1a containing homomeric or heteromeric channels, including homomeric ASIC1a, and heteromeric ASIC1a/2a and ASIC1a/2b channels. The inhibition of the homomeric ASIC1a channel by Triol in CHO cells suggests that Triol should inhibit ASIC channels in cortical neurons. As expected, Triol exhibits a similar inhibitory activity on ASIC currents in primary cultured mouse cortical neurons (FIG. 2A-B). As shown in FIG. 2A, a time-dependent decrease of the currents was observed when Triol (10 μM) was applied. The currents were decreased by ~40% within 5 min of application (n=5, *$p<0.05$ and **$p<0.01$ compared with the vehicle). This inhibition is also irreversible even after 30 min washout (data not shown), which is consistent with the findings observed in the CHO-1a cell line. In contrast, the application of the vehicle for 5 min did not cause a significant effect on ASIC currents in mouse cortical neurons. These results are consistent with those observed in CHO-ASIC1a cells. Since the heteromeric ASIC1a-containing channels are indistinguishable from ASIC1a homomeric channels in apparent proton sensitivity of activation and inactivation kinetics, the inhibited ASIC1a-like currents by Triol may come from homomeric or heteromeric ASIC1a channels.

Structure-Activity Relationship Analysis

The study further explored the structure and activity relationship of Triol on ASIC currents in primary cultured mouse cortical neurons. The effects of Triol and its metabolic precursors, including cholesterol, 5α,6α-epoxycholesterol (5α,6α-epoxy-Chol), 5β,6β-epoxycholesterol (5β,6β-epoxy-Chol), and synthetic analog 5α-androst-3β, 5, 6β-triol (Andro-triol) on ASIC currents were compared (FIG. 2C). Our data demonstrated that none of these analogs, except Andro-triol, showed a significant effect on ASIC currents (FIG. 2D-F). Andro-triol slight decreases ASIC current (FIG. 2E-F, n=3, *$p<0.05$). These data suggest that the hydroxyl groups at positions 5 and 6 on the A/B ring are important functional groups. The change of the two hydroxyl groups to epoxides, e.g., in analogs 5α,6α-epoxy-Chol and 5β,6β-epoxy-Chol, and double bonds, e.g., cholesterol, results in complete loss of the activity on ASIC (FIG. 2C-E). In addition, the removal of the side chain results in analog Andro-triol, which also shows no significant effect on ASIC1a (FIG. 2E-F), suggesting that the side chain is also critical for its inhibitory activity.

Triol Inhibits ASIC1a Current in a Use-Dependent and Voltage-Independent Manner

Figure 3:
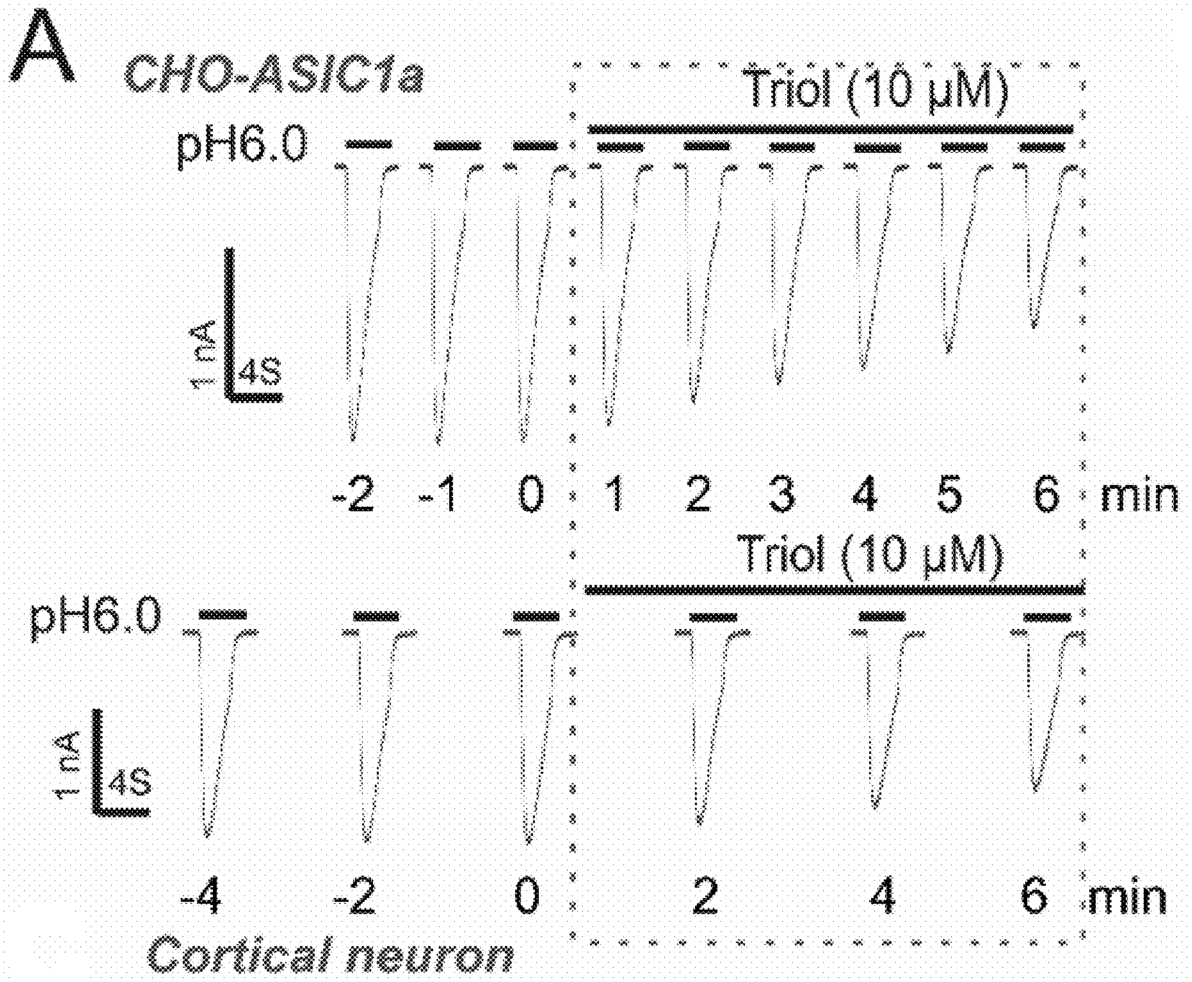
FIG. 3 shows inhibition of ASIC1a currents by Triol in a use-dependent, and voltage-independent manner. (A) Representative current traces show the inhibition of ASIC1a currents by Triol (10 μM) under different stimulating frequencies (once every minute or once every two minutes). (B) Summary data showing the use-dependent (or frequency-dependent) inhibition of ASIC1a peak currents by Triol (n=4-5, *p<0.05, **p<0.01 compared with the peak currents recorded at lower frequency, two-way ANOVA). (C-D) Representative current traces and summary data shows the inhibitory effect of Triol on ASIC at different holding membrane potentials of −60 and −30 mV, in primary cultured mouse cortical neurons. (E-F) Representative traces and summary data showing that the effect of Triol (10 μM) on the pH-dose response relationship of the ASIC peak currents in primary cultured mouse cortical neurons, before and after perfusion of Triol for 5 min. (G-H) Representative traces and summary data show that the current-voltage relationship before (Before Triol) and after perfusion of Triol for 5 min (After Triol).
Figure 3:
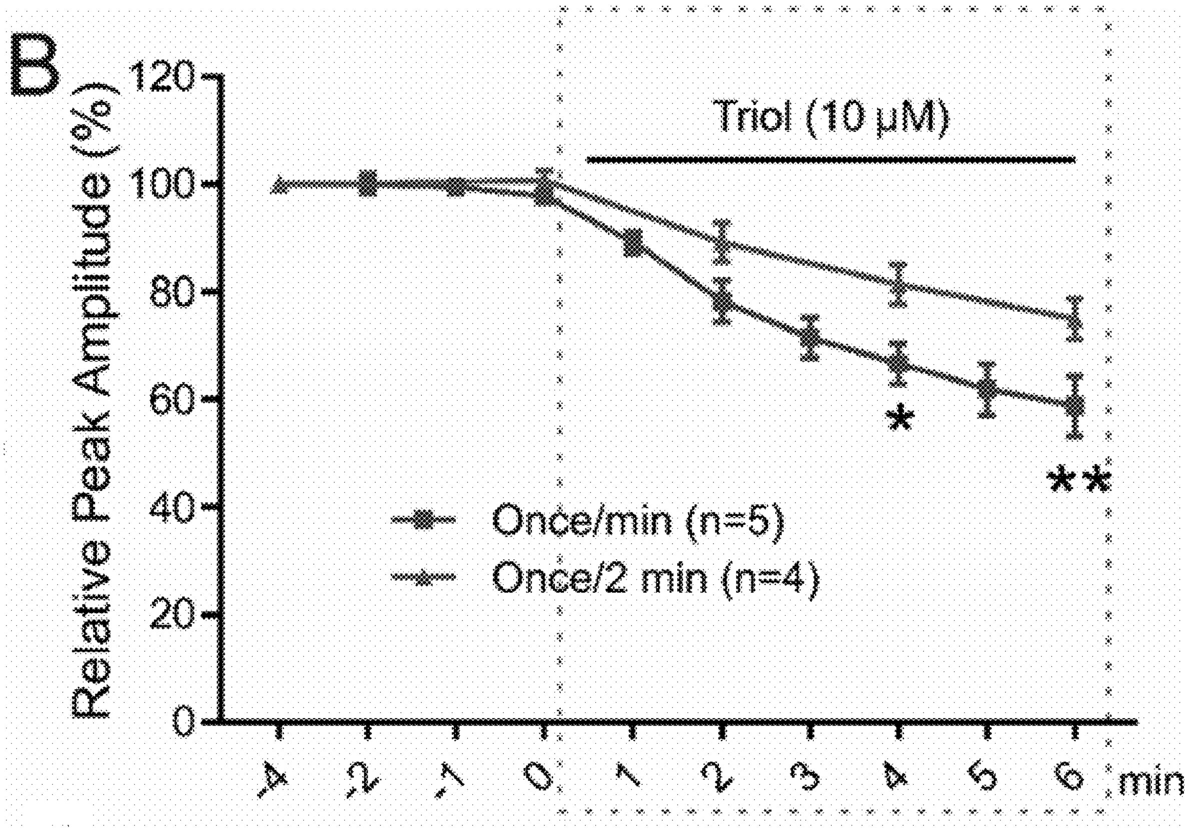
Figure 3:
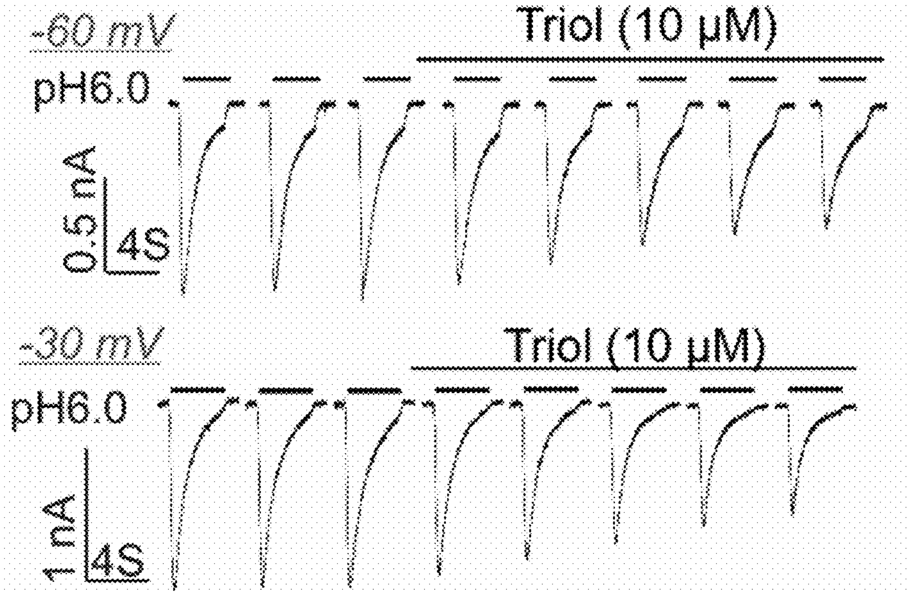
Figure 3:
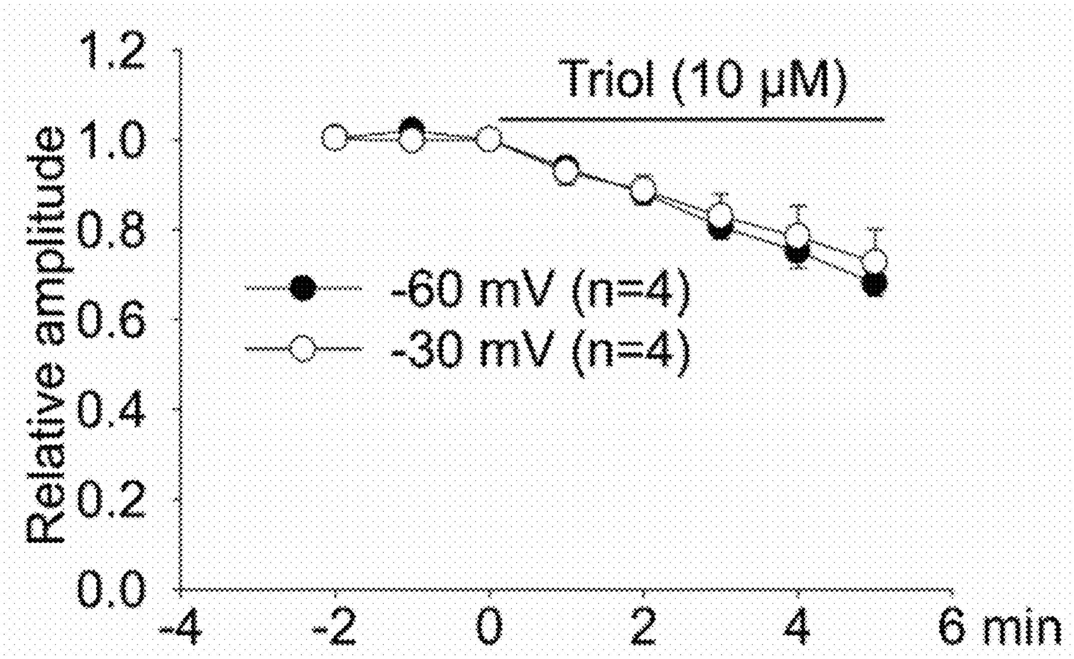
Figure 3:
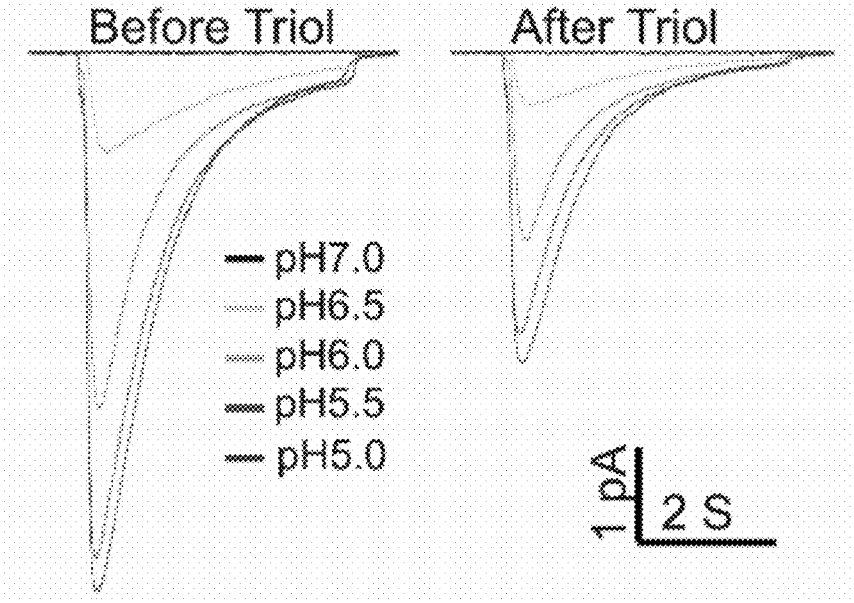
Figure 3:
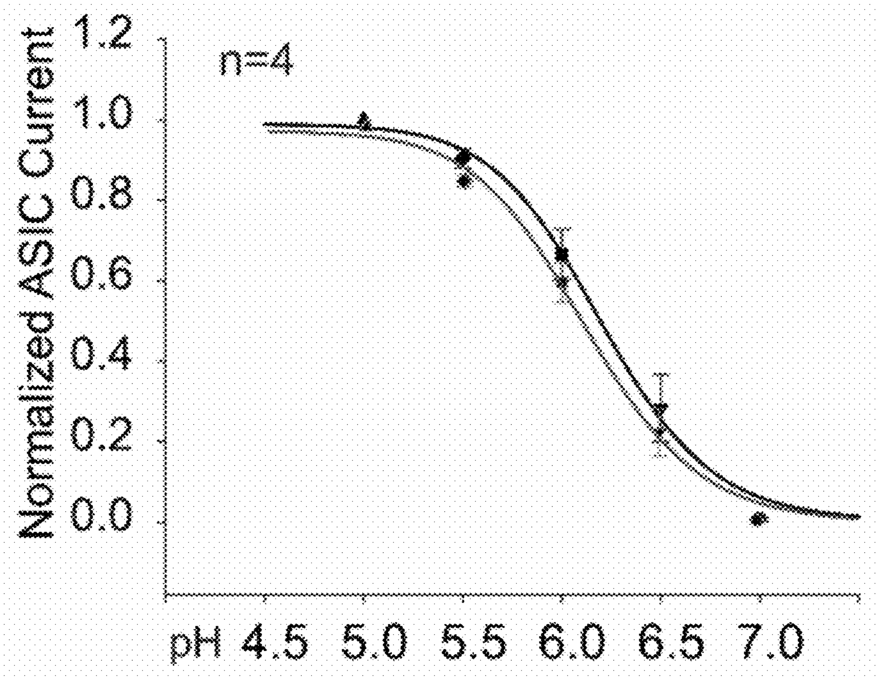
Figure 3:
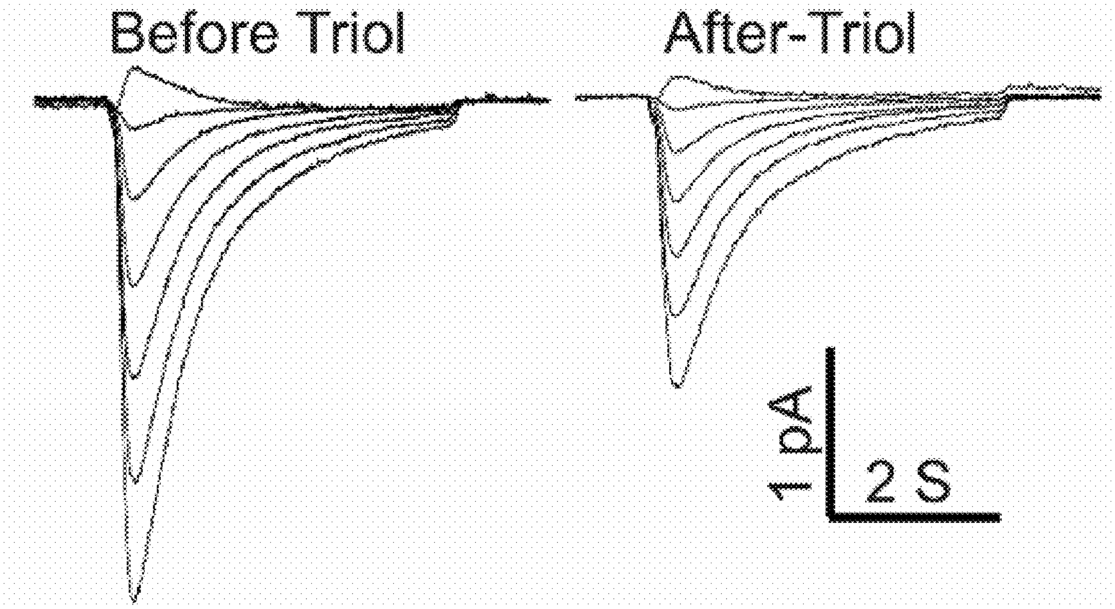
Figure 3:
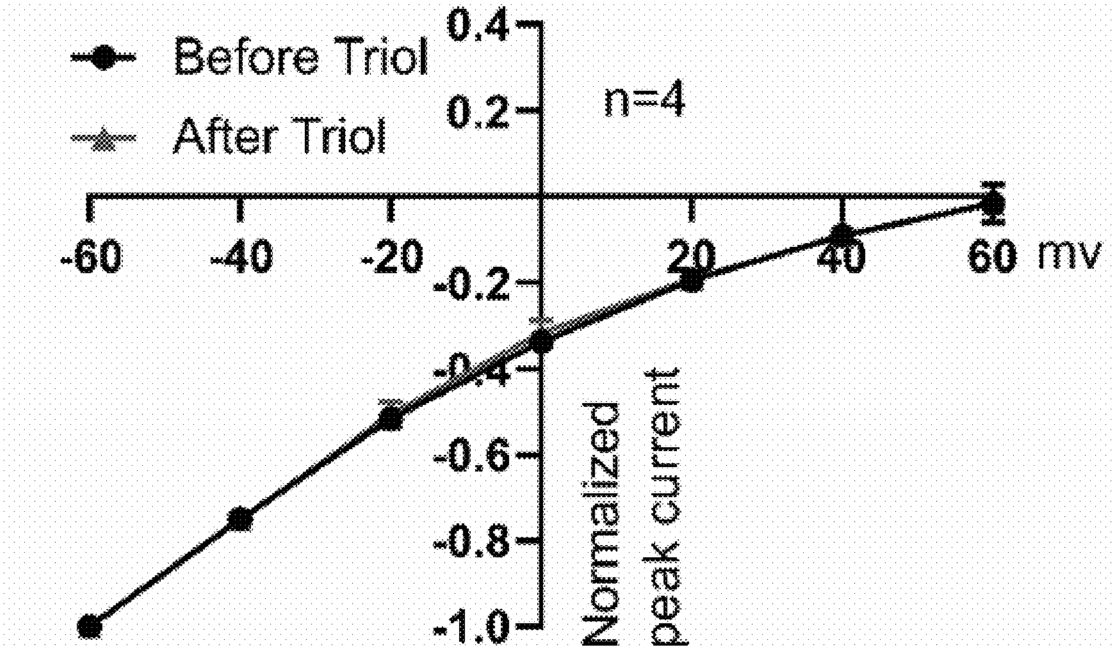

The time-dependent inhibition of ASIC1a by Triol suggests a use-dependent (also known as frequency-dependent) inhibition. To test this hypothesis, the study compared the degree of inhibition of ASIC1a currents by Triol under two different stimulatory frequencies of once every one minute and once every two minutes. As shown in FIG. 3A and B, within 5 min of recording, Triol inhibited ~20% of ASIC1a currents at a lower stimulatory frequency (once/two min). In comparison, it inhibited ~40% of the ASIC current at a higher stimulatory frequency (once/one min) (n=4-5, *$p<0.05$ and $p<0.01$), suggesting a use- or frequency-dependent inhibition of ASIC1a. In addition, the study also determined whether Triol inhibits ASIC1a in a voltage-dependent manner. The study compared the inhibitory activity when the membrane was clamped at a resting membrane potential of −60 mV or depolarized potential of −30 mV. The study found no significant change in the inhibitory activity of Triol (FIG. 3**C-D), suggesting that Triol inhibits ASIC in a voltage-independent manner.

To have a better understanding of the mechanism, the study examined whether Triol inhibits ASIC by affecting the proton affinity or modifying the current-voltage relationship (IV). Triol was perfused for 5 min, which inhibits ~40% of ASIC current (FIG. 3E-H). As shown in FIG. 3E-F, there is not a significant shift in the pH dose-response, suggesting that Triol does not affect the affinity of proton binding to ASIC. The study also found that the IV curves overlap before and after Triol inhibition, implying that Triol does not affect the current-voltage relationship (FIG. 3G-H).

Triol Inhibits Heteromeric ASIC1a-Containing Channels

The primary cultured cortical neurons express ASIC1a, 2a, and 2b. ASIC1a is a predominant subunit, which can form homomeric ASIC1a or heteromeric ASIC1a/2a and ASIC1a/2b channels. Considering that the homomeric ASIC2a channels are insensitive to pH 6.0, and ASIC2b does not form functional channels, the ASIC currents activated by pH 6.0 in the cortical neurons might be from homomeric ASIC1a, heteromeric ASIC1a/2a, ASIC1a/2b, or a combination of these channels. In these regards, the Triol may inhibit heteromeric ASIC1a/2a or ASIC1a/2b channels.

Figure 4:
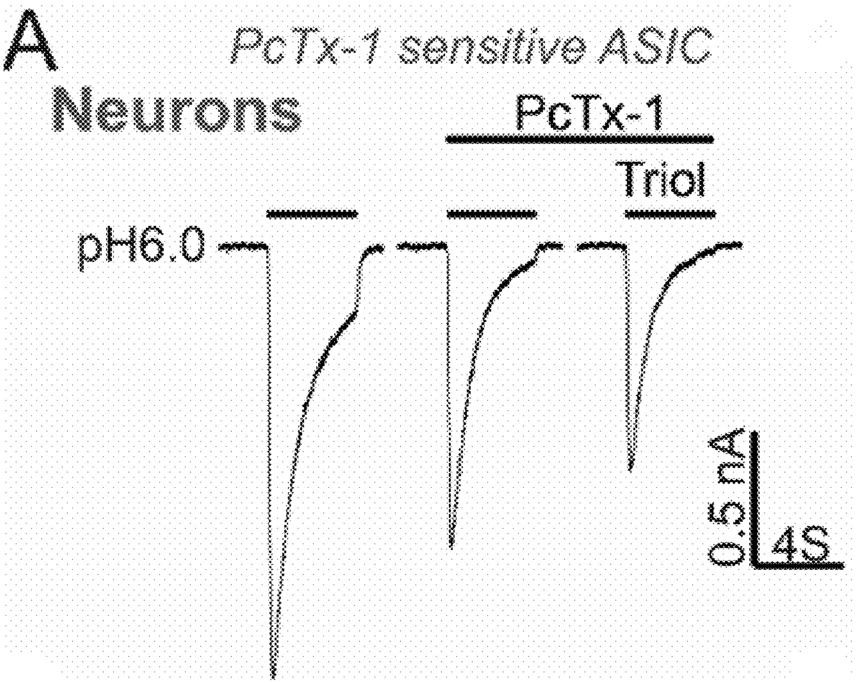
FIG. 4 shows inhibition of the heteromeric ASIC1a containing channel by Triol. The effect of Triol (10 μM) on the remaining ASIC currents after inhibition by PcTx1 (40 nM). (A-B) Representative traces and summary data showing the effect of Triol on ASIC currents in the presence of PcTx-1 in PcTx-1 sensitive cortical neurons (n=9, p<0.01), and (C-D) PcTx1 insensitive ASIC currents (n=3, p<0.01). (E-F) The effect of PcTx-1 on ASIC currents in the presence of Triol (10 μM) (n=4) in cultured cortical neurons. (G-H) The effect of PcTx1 (40 nM) on ASIC currents in CHO-ASIC1a stable cell line (CHO-ASIC1a) (n=3, p<0.01, student's t-test). (I-J) Effect of Triol (10 μM) on ASIC currents, in the presence of PcTx-1, in PcTx-1 sensitive CHO-ASIC1a stable cell line with transient expression of ASIC2a-GFP, and (K-L) in PcTx1 insensitive cells (n=4 or 5, p<0.01, student's t-test).
Figure 4:
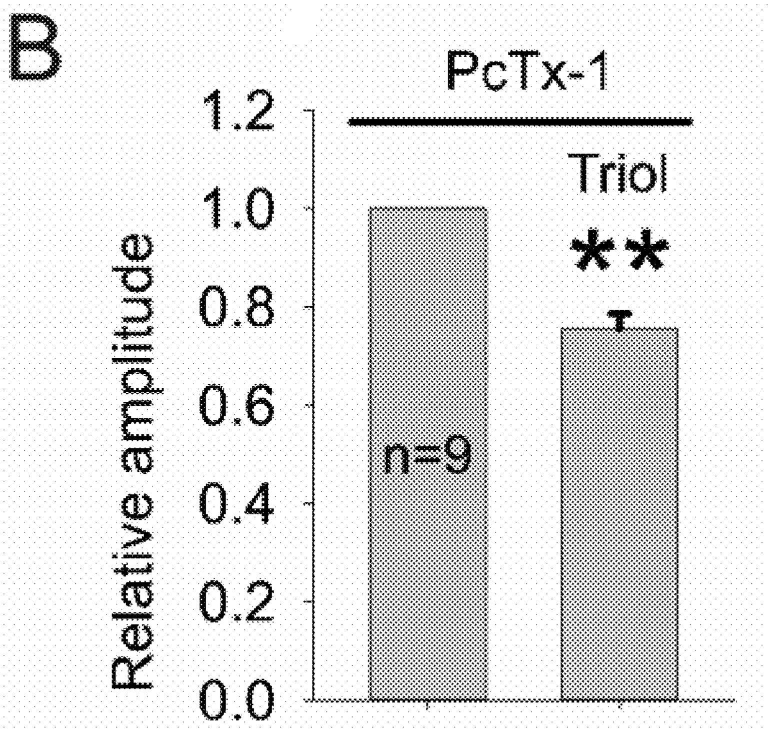
Figure 4:
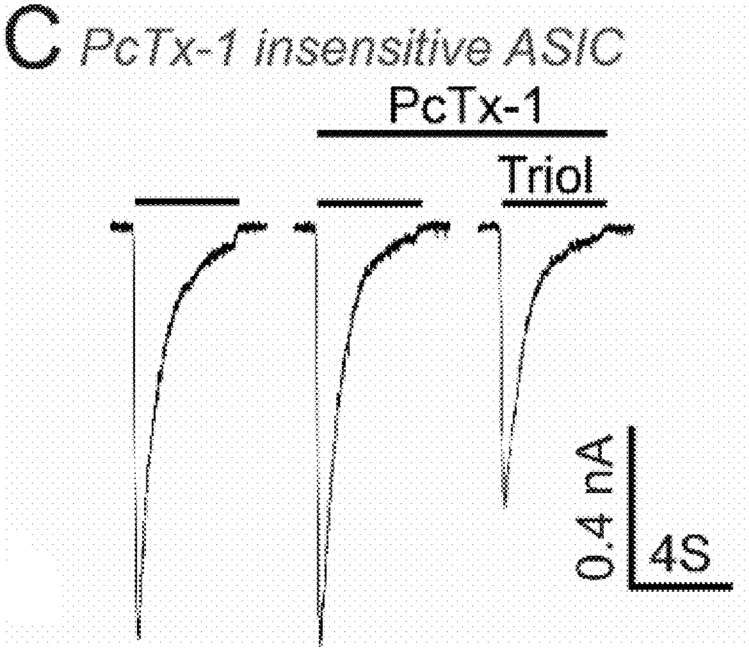
Figure 4:
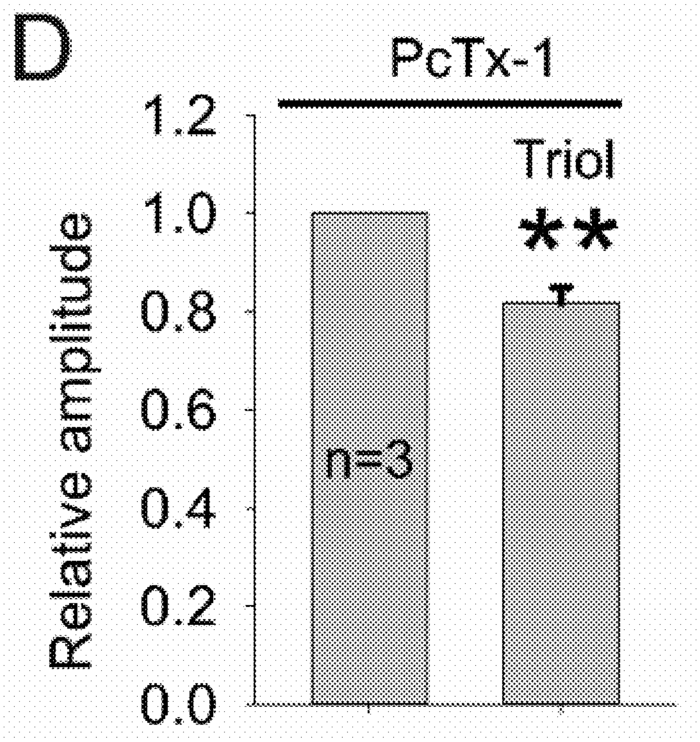
Figure 4:
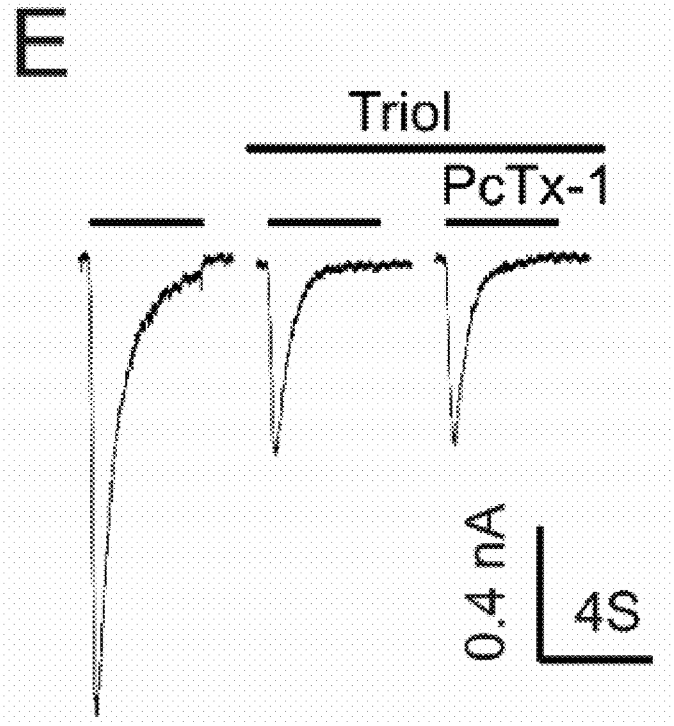
Figure 4:
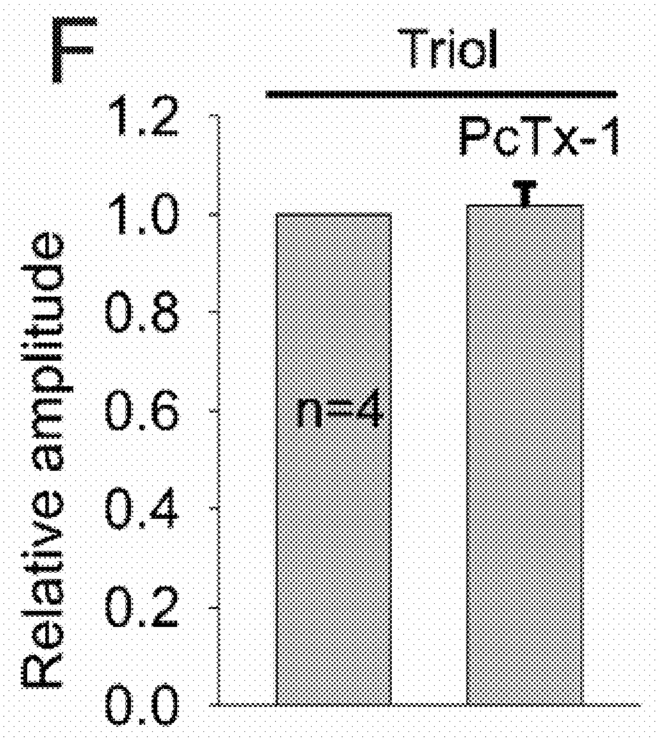
Figure 4:
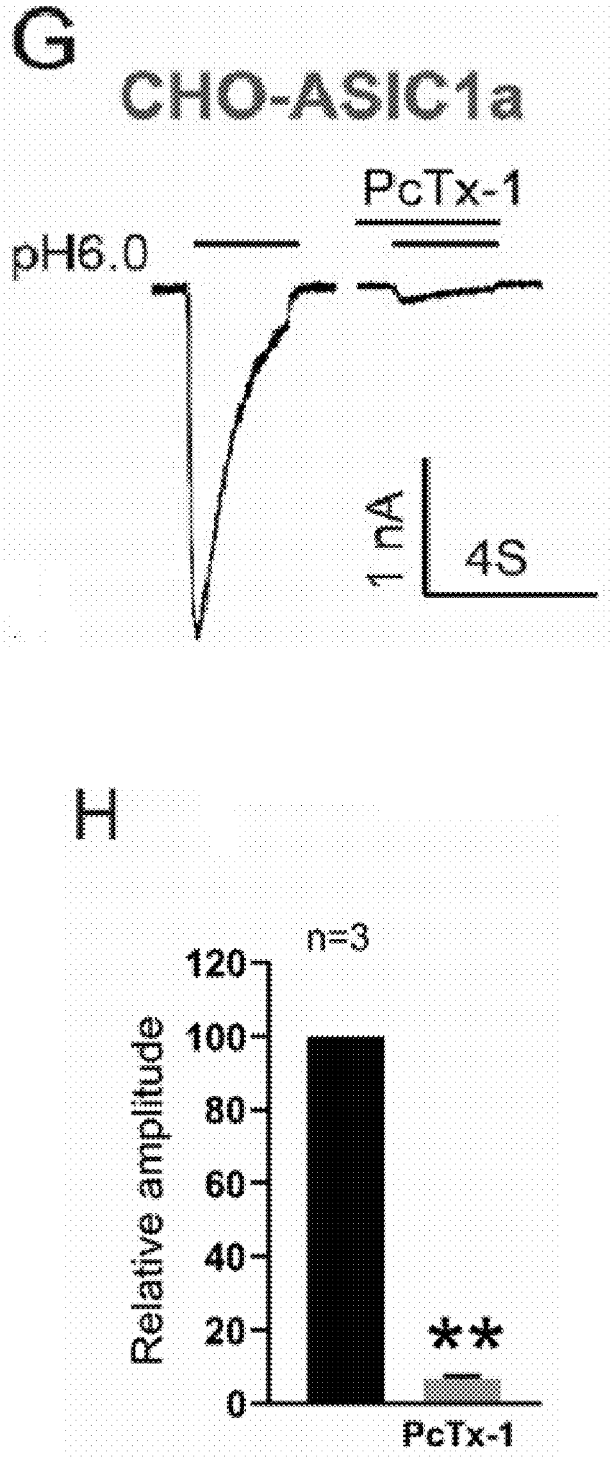
Figure 4:
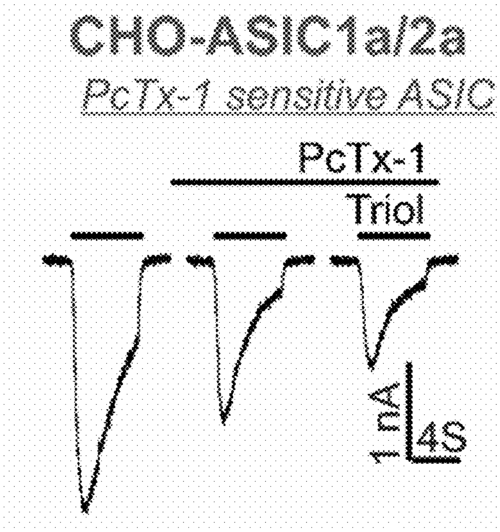
Figure 4:
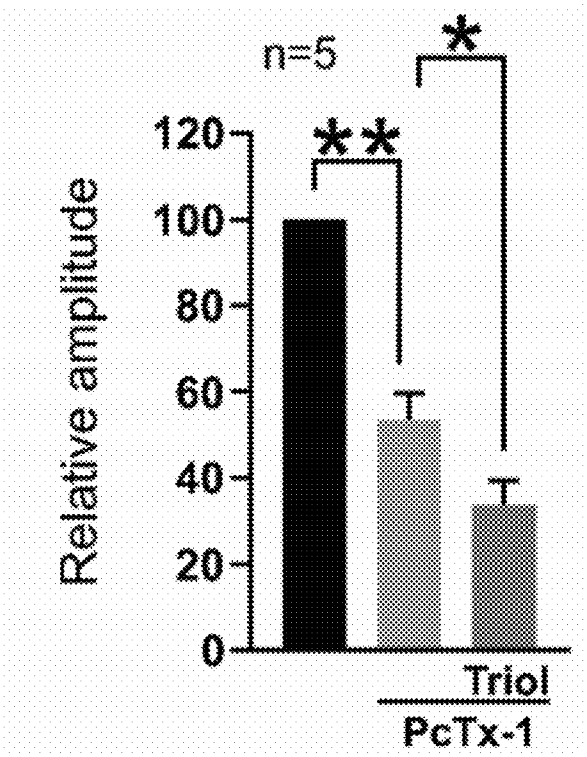
Figure 4:
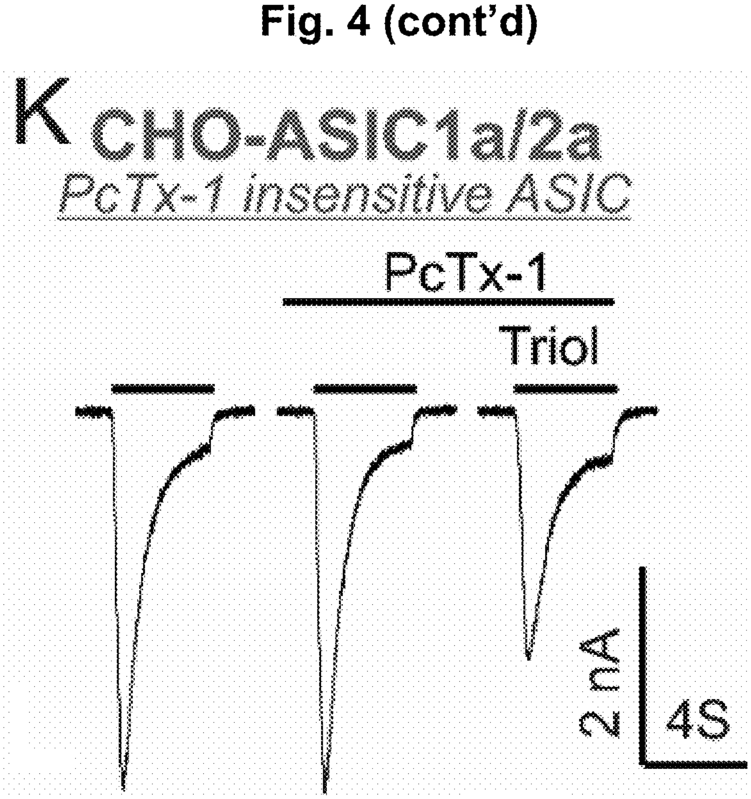
Figure 4:
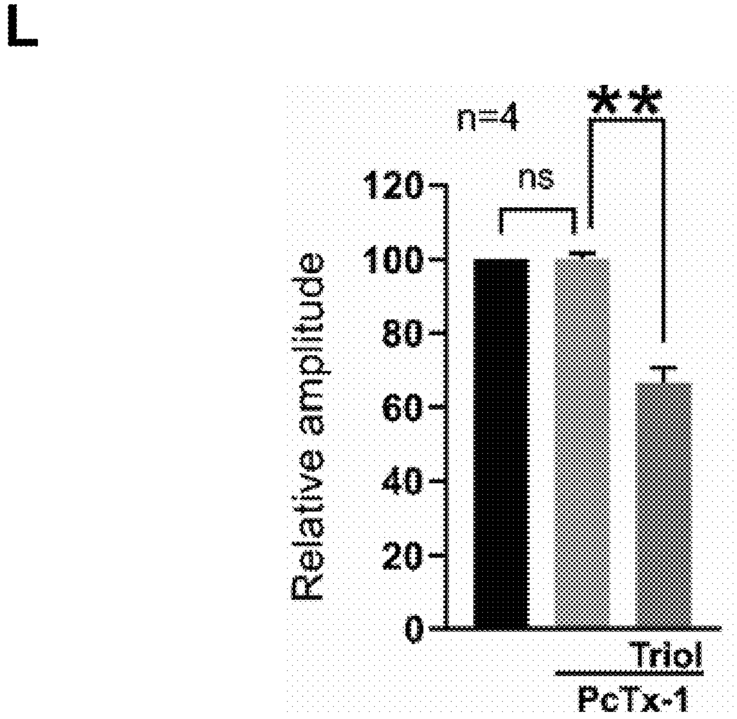

First, the study determined whether Triol inhibits ASIC1a/2a heteromeric channels. It has been shown that PcTx-1 is a potent and specific inhibitor for homomeric ASIC1a and heteromeric ASIC1a/2b channels, but not for ASIC1a/2a channels. To determine whether Triol inhibits ASIC1a/2a channels, the study used a saturating concentration of PcTx1 (40 nM) to inhibit ASIC1a channels and ASIC1a/2b channels. The study found that ASIC currents in the majority of the neurons (9 of 12 cells) are sensitive to PcTx1 blockade, suggesting expression of the homomeric ASIC1a or heteromeric ASIC1a/2b channels, and the remaining ASIC currents should come from ASIC 1 a/2a channels. The study found that the remaining currents in the presence of PcTx1 could be further inhibited by Triol (FIG. 4A-B). The ASICs in other neurons (3 of 12 cells) are insensitive to PcTx-1 inhibition, suggesting the expression of ASIC1a/2a channels but not homomeric ASIC1a and ASIC1a/2b channels (FIG. 4C-D). Triol could still inhibit these currents, suggesting that Triol also inhibits heteromeric ASIC1a/2a channels. In contrast, in the presence of Triol, PcTx-1 causes no more inhibition of the ASIC currents in all the recorded neurons (FIG. 4E-F), suggesting that Triol largely suppresses all the PcTx1 sensitive currents, including those of homomeric ASIC1a and heteromeric ASIC1a/2b channels.

To provide additional evidence that Triol inhibits heteromeric ASIC1a/2a channels, we expressed ASIC2a-GFP in CHO-ASIC1a stable cell line. Only the GFP-positive cells were recorded. The GFP-positive CHO-1a cells may express a mix of homomeric ASIC1a, ASIC2a, or heteromeric ASIC1a/2a channels. Since homomeric ASIC2a channels are not activated at pH 6.0 37, the ASIC currents activated at pH 6.0 might be due to the activation of ASIC1a or ASIC1a/2a channels. To exclude the contamination of the ASIC1a channel, the study used a saturating concentration of PcTx-1 to inhibit the ASIC1a currents (FIG. 4G-H). In ASIC2a-GFP positive cells, after PcTx-1 blockage, the remaining currents should be mediated by ASIC1a/2a, which could be inhibited by Triol (FIG. 4I-J, n=5, *p<0.05 and p<0.01). The study also found that the ASIC currents activated at pH 6.0 in some cells (4 of 9 cells) are not sensitive to PcTx-1, suggesting the expression of heteromeric ASIC1a/2a channels. Triol inhibited these currents (FIG. 4K-L, n=4, p<0.01). These data in the heterogenous expression system further suggest that Triol can inhibit heteromeric ASIC1a/2a channels.

Triol Attenuates Acidosis-Induced Cytotoxicity In Vitro

Figure 5:
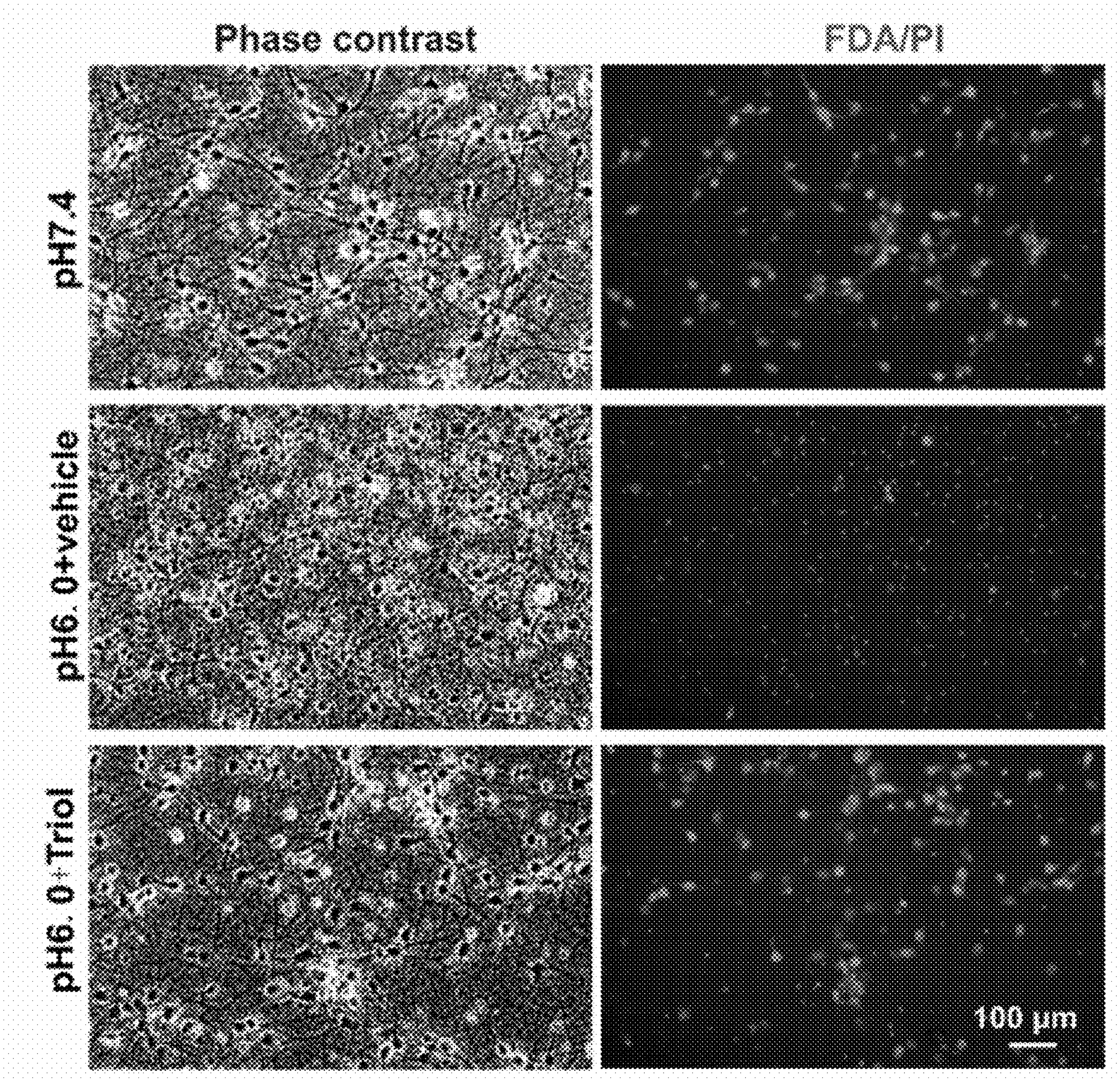
FIG. 5 shows the effect of Triol on acidosis-induced cytotoxicity in primary cultured cortical neurons. Viability and cytotoxicity in primary cultured mouse cortical neurons were measured at 24 h after acid treatment by fluorescein diacetate (FDA) and propidium iodide (PI) staining and LDH assays. (A) Representative phase-contrast images (left panel), and FDA (green)/PI (red) staining images (right panel) of alive/dead neurons at 24 h after treatment with pH 6.0 solutions for 1.5 h in the presence or absence of Triol (10 μM). (B-C) Summary data show different concentrations of Triol (1 and 10 μM) effectively increase survival rate and decrease death rate of cortical neurons, as counted by FDA and PI staining respectively (*p<0.05 and p<0.01 compared with the vehicle group, n=3-5, one-way ANOVA). (D-E) Summary data show LDH release following acid treatment in the presence or absence of Triol or its analogs, including 5α,6α-epoxycholesterol (5α,6α-epoxy-Chol), 5β,6β-epoxycholesterol (5β,6β-epoxy-Chol), and 5α-androst-3β, 5, 6β-triol (Andro-triol) (p<0.01 versus pH 6.0, n=7-8, one-way ANOVA).
Figure 5:
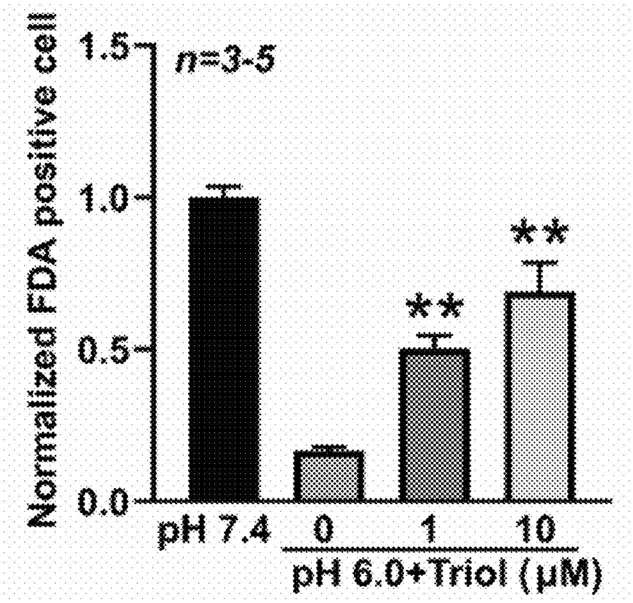
Figure 5:
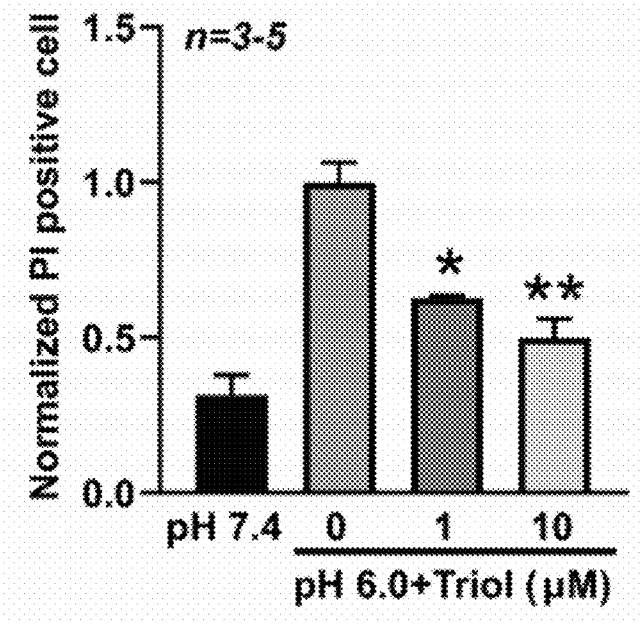
Figure 5:
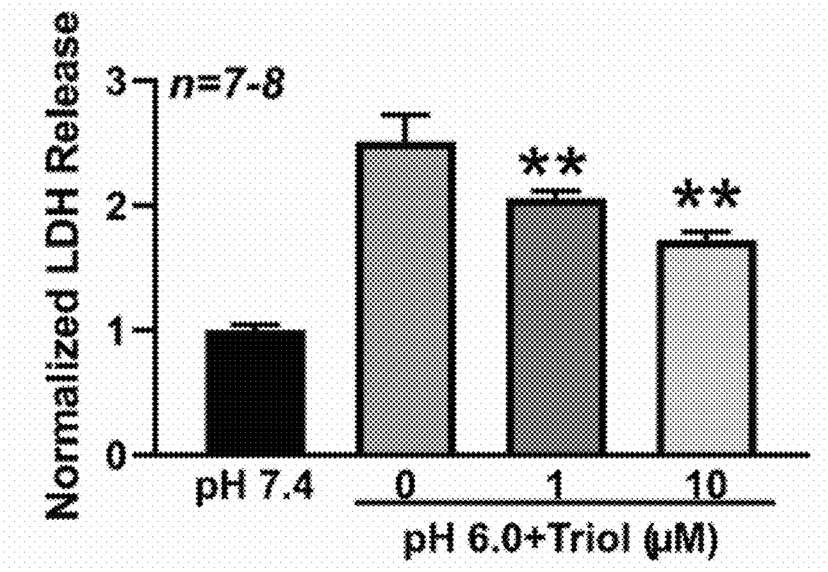
Figure 5:
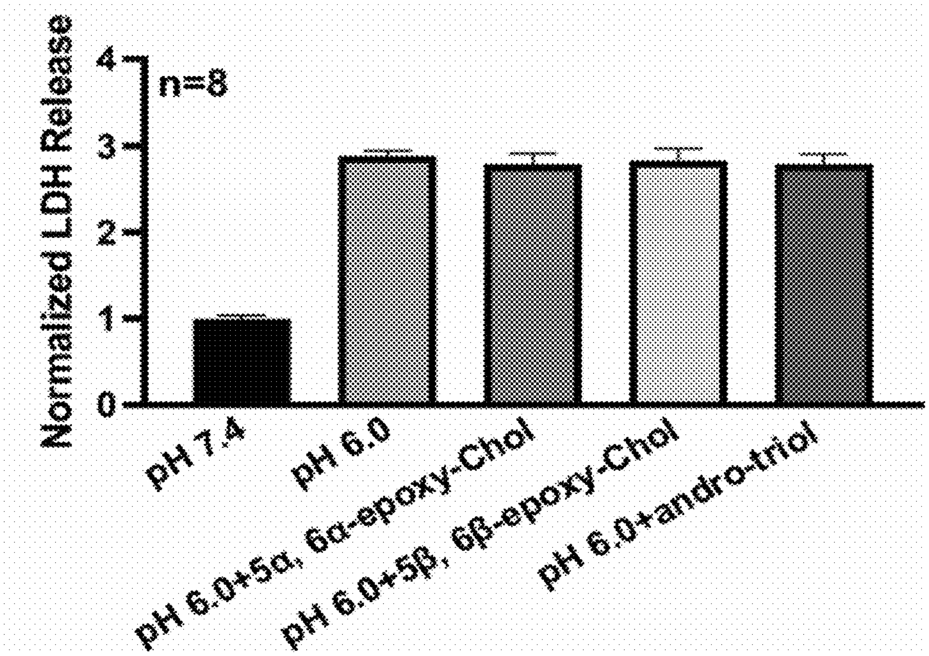
Figure 6:
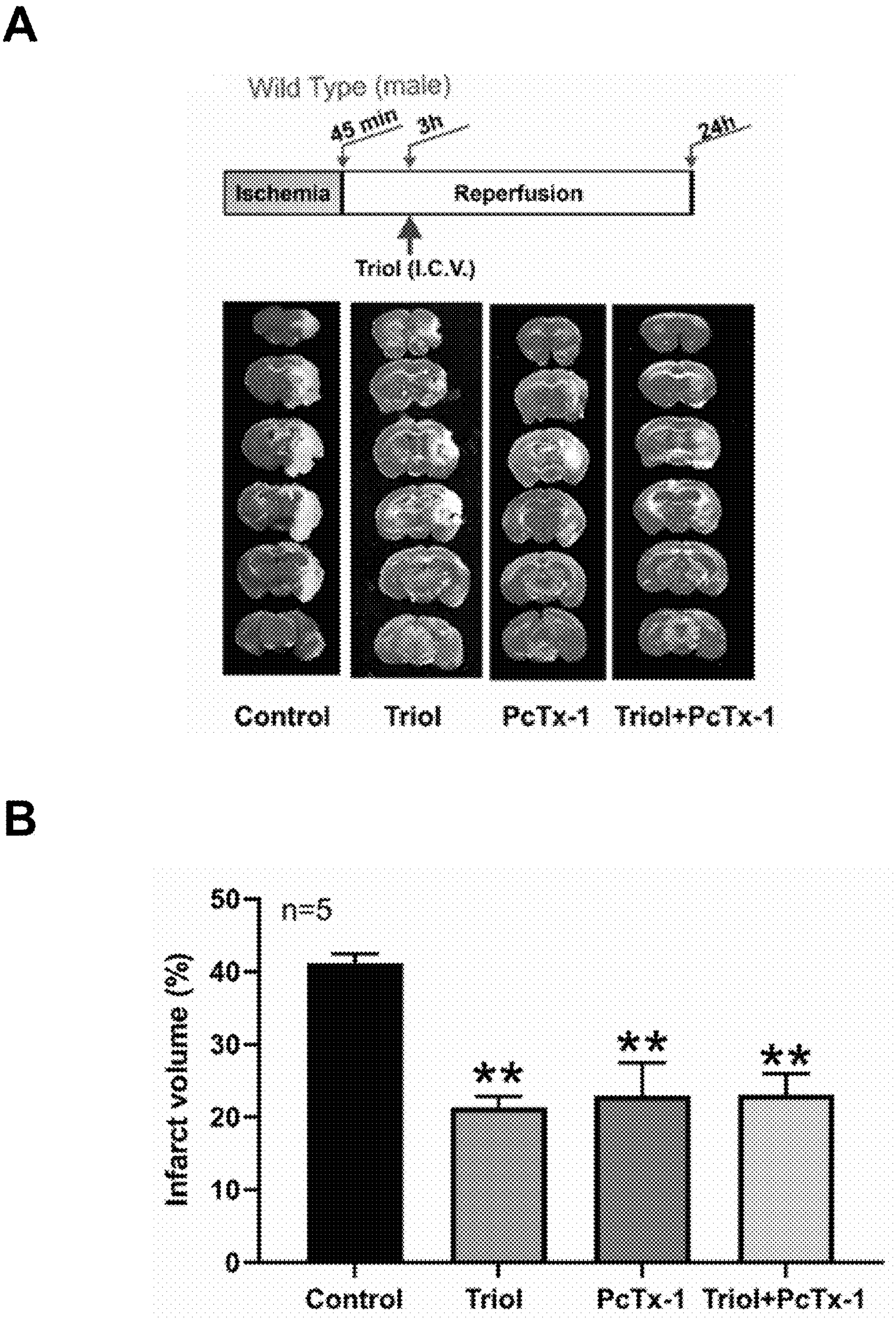
FIG. 6 shows the effect of ASIC1a blockade and ASIC1a or 2a knockout on the protective activity of Triol in ischemic brain injury. Triol (stock solution, 400 μM) or vehicle (stock solution, 20% HP-β-CD) were administrated through intracerebroventricular (ICV) injection at 3 h after 45 min MCAO with or without co-application of PcTx-1 (stock solution, 1 μM). (A) Representative TTC staining images of brain slices and (B) summary data showing the infarction volume of wild male mice brain at 24 h after MCAO (n=5, **p<0.05 compared with vehicle control). (C-E) Representative TTC staining images of brain slices and summary data showing the infarction volume of mice brain after MCAO in the presence or absence of Triol in male and female ASIC1a-knock out mice (n=6). (E) summary data showing the infarction volume of mice brain after MCAO in the presence or absence of Triol in male ASIC2a-knock out mice (n=4, *p<0.05).
Figure 6:
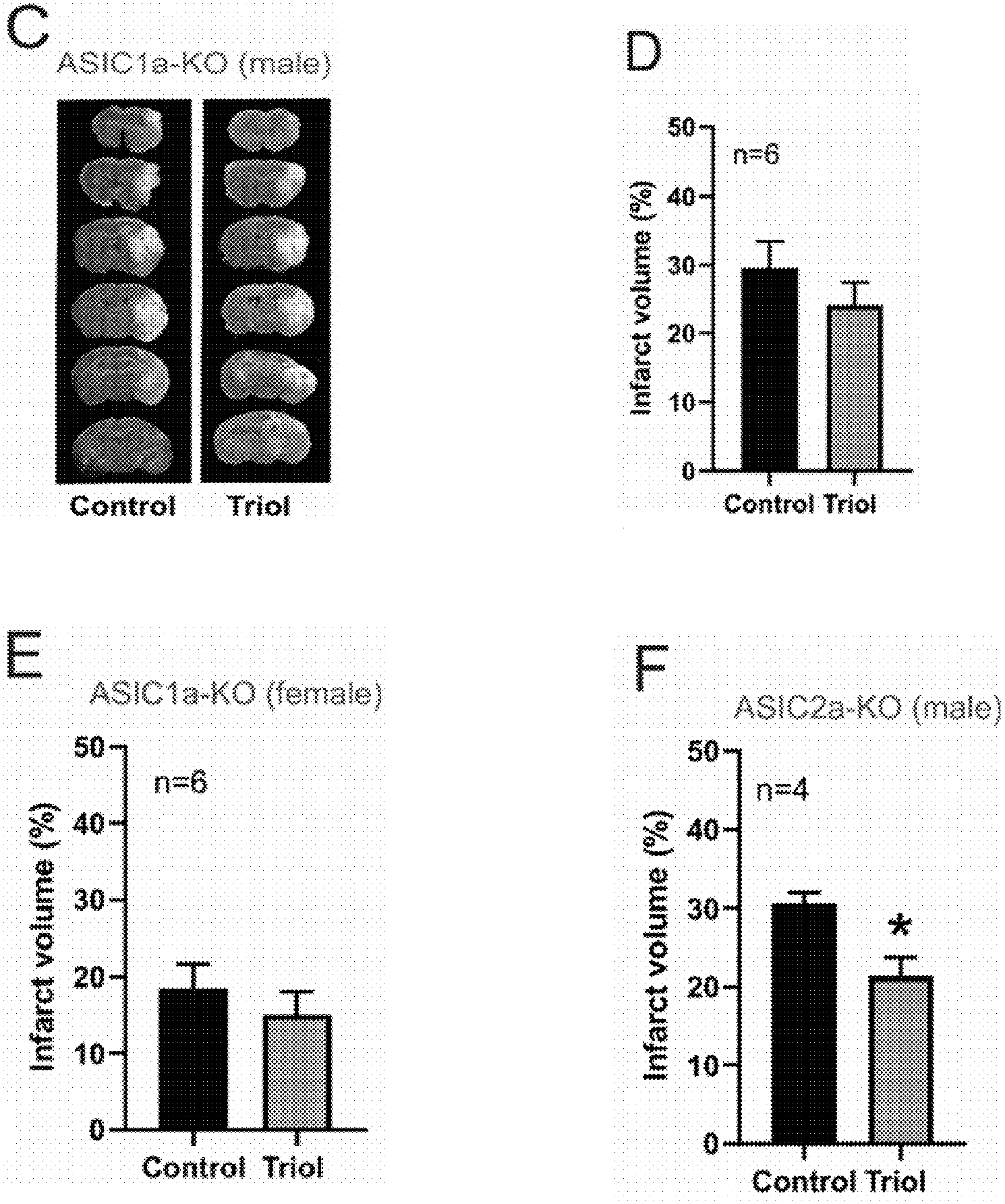

It has been shown that activation of ASIC1a-containing channels, including homomeric ASIC1a and heteromeric ASIC1a/2b contributes to acidosis-induced neuronal injury in vitro and in vivo. Regarding the inhibitory effect of Triol on homomeric ASIC1a and heteromeric ASIC1a/2b channels, Triol may protect against acidosis-induced neuronal injury. To test this hypothesis, the study examined the effect of Triol on acid-induced neuronal injury in primary cultured mouse cortical neurons. Cell death was assessed by fluorescent staining of live cells with FDA (green fluorescence) and dead cells with PI (red fluorescence). Cellular cytotoxicity was also determined by LDH assay. To avoid the potential involvement of NMDAR, MK-801 (10 μM), a specific blocker of NMDAR, was added. Acid incubation (pH 6.0) for 1.5 h dramatically reduced cell viability, as demonstrated by the reduced number of FDA-positive cells and increased number of PI-positive cells (FIG. 5A). Triol (1 and 10 μM) inhibited the cell death in a concentration-dependent manner (FIG. 5A-C, n=3-5, *p<0.05 and p<0.01). Consistently, the LDH assay shows that Triol significantly decreased acid-induced cytotoxicity (FIG. 5D, n=7-8, p<0.01), suggesting a neuroprotective effect. To provide insight into the structure-activity relationship, we also examined the effect of its analogs, including 10 μM 5α,6α-epoxy-Chol, 5β,6β-5β,6β-epoxy-Choi, and Androtriol on the acid-induced neuronal injury. The study found that none of them shows significant protection (FIG. 5E, n=8).

Triol Protects Against Ischemic Brain Injury Through Inhibition of ASIC1a

It has been shown that Triol inhibits NMDAR, which might be one of the mechanisms underlying its protective activity in ischemic stroke. However, this mechanism cannot well explain the long therapeutic time window of at least 4 h because the blockade of NMDA receptor has a shorter therapeutic time window of less than 2 h. Considering the inhibitory effect of Triol on ASIC1a and ASIC1a/2b, which play a critical role in acidosis- and ischemia-induced neuronal injury, blockade of ASICs might be a potential mechanism underlying Triol's protective activity in ischemic stroke. Blockade of ASIC1 provides a therapeutic time window of 5 h. To avoid contamination by NMDA blockade, the study applied Triol at 3 h following 45 min MCAO. The study compared the protective effect of Triol in the presence or absence of ASIC1a-specific inhibitor PcTx-1. A total of 1 μl artificial CSF (aCSF)-containing PcTx-1 (400 nM) or Triol (400 μM) was injected. The CSF volume for adult mice is estimated to be ~40 μl 41. Assuming that the infused Triol is uniformly distributed in the CSF, the estimated concentrations of ~40 nM PcTx-1 or 10 μM Triol are expected. As anticipated, the infarct volume was significantly reduced by PcTxl (FIG. 5A-B, n=5, **p<0.01 compared with control). Similar protection is observed in Triol-treated mice. Interestingly, in the presence of PcTx-1, there is no additional reduction of the infarct volume by Triol, suggesting that the protective activity of Triol is dependent on the presence of ASIC1a (FIG. 5A-B).

To provide further evidence that Triol protects against ischemic brain injury through the blockade of ASIC1a, the study examined its protective activity in ASIC1a knockout mice. The infarct volume in male ASIC1a knockout mice was dramatically reduced (FIG. 5C-D) compared with that in wild-type mice (FIG. 5A-B). Triol didn't show additional protection against ischemic brain injury in male ASIC1a knockout mice (FIG. 5C-D, n=6). A similar result was observed in female ASIC1 knockout mice (FIG. 5E), suggesting no sex difference. In contrast, Triol provides significant protection in ASIC2 knockout mice (FIG. 5F, n=4, *p<0.05). In these mice, there is a predominant expression of homomeric ASIC1a channels in the brain due to the loss of ASIC2 in ASIC2 knockout mice. The protection by Triol might be due to the inhibition of homomeric ASIC1a channels. Collectively, the in vivo data strongly suggest that the inhibition of ASIC1a activity is an important mechanism underlying the neuroprotective effect of Triol in ischemic brain injury.

Example 2: Treatment of Depression

Based on the fact that Triol inhibits ASIC1a, Triol can have anti-depression activity. This study shows the anti-depression activity of Triol. A mouse model of depression induced by repeated corticosterone injections is used. Depression-like behaviors are induced by repeated administration of corticosterone (40 mg/kg, i.p.), once a day for 21 days in mice. Mice arerandomly assigned to 4 experimental groups (n=10/group). Control, corticosterone, corticosterone+Vehicle (20% HP-β-CD) and corticosterone+Triol (12 mg/kg, i.p.). Triol is administered daily. The sucrose consumption test, open-field test (OFT), tail suspension test (TST), and forced swimming test (FST) are used to evaluate the therapeutic effect of Triol. Corticosterone treatment induced depression-like behaviors, including increased immobility time in the TST, OFT, and FST, decreased time of movements in OFT, and decreased sucrose consumption. Triol shows antidepressant activity, which is evident by alleviating corticosterone-induced depression-like behaviors.

Sucrose Preference and Chronic Mild Stress

Sucrose preference is assessed in individually housed, stressed and unstressed mice. Briefly, two bottles (one 8% sucrose and one water) are placed in each cage for 3 d; 2 d to habituate and 1 d to assess sucrose preference. The locations of the bottles are rotated each 24-h period. At the beginning and end of the final 12-h period both bottles are weighed, and sucrose preference is defined as sucrose solution consumed/total liquid consumed×100%. Unstressed mice only undergo the 3 d sucrose preference assessment. Stressed mice also undergo 6 d of unpredictable stressors in the following order: restraint (3 h), wetted bedding (12 h), restraint (3 h), 45° angle cage tilt (12 h), paired housing with an unfamiliar mouse (1 h), exposure to a predator odor (1 h) (trimethylthiazoline, Pherotech International). Sucrose preference is then assessed during the final overnight period as described above.

Tail Suspension Test

This test is performed by the Tennessee Mouse Genome Consortium (tnmouse.org/neuromutagenesis/behavioral). Mice are suspended by the tail from a ledge ~60 cm from the ground with adhesive tape. Immobility is defined as the absence of movement and is scored over a 6-min trial.

Forced Swim Test

Mice are placed in a 4000 ml beaker filled with 3500 ml of water (25 °C) and video taped during a 6 min trial. Immobility time is scored by a blinded experimenter and is defined as absence of motion except that required to keep head above water (Heinrichs and Koob, 2005). Fluoxetine (3 mg/kg, i.p.), desipramine (2 mg/kg, i.p.), and bupropion (2 mg/kg, i.p.) are each delivered 30 min before the forced swim test (FST). P-chlorophenylalanine methyl ester (PCPA; 300 mg/kg, i.p.) is injected daily for 3 d before the FST (Heurteaux et al., 2006). PcTx venom, PcTx1 peptide, and A-317567 are injected by intracerebroventricular cannula (described below).

Whole-Cell Voltage Clamp Recordings

Cortical neurons are obtained from 1-2 d old pups and cultured for 8-14 d. Whole-cell voltage-clamp recordings are obtained at 20-23 °C using an Axopatch 200B amplifier and Clampex 8.2 (Axon Instruments) sampled at 200 μs interval and filtered at 2 kHz. Extracellular pH is changed with a rapid solution changer (RSC-200; Biologic). Membrane voltage is maintained at −70 mV. Bath solutions contained (in mm): 100 NaCl, 5.4 KCl, 2 CaCl2, 1 MgCl2, 10 HEPES, 10 MES, and pH is adjusted with TMA·OH. Patch pipettes (3-5 MSΩ) contained (in mm): 10 NaCl, 70 K-gluconate, 10 KCl, 1 MgCl2, 10 EGTA, 25 HEPES, and 3 Na2ATP, adjusted to pH 7.3 with KOH. A-317567 (kindly provided by Drs. Alan Light and Jon Rainier, University of Utah, Salt Lake City, UT) is suspended in 5% DMSO in deionized water for a 10 mm stock and diluted in the bath solutions to a final concentration of 45 μm.

Intracerebroventricular Surgeries and Injections

Intracerebroventricular guide cannulae are implanted into the left lateral ventricle of anesthetized mice (0.3 mm caudal, 1.0 mm lateral, 3.0 mm ventral with respect to bregma) (Coryell et al., 2007). Cannulae are fixed to the skull with dental cement and an anchoring screw. Two to four days later, 5 μl PcTx venom (9 ng/μl -24 h before testing), PcTx1 peptide (100 nm-90 min before testing), or A-317567 (1 mm-90 min before testing) in sterile artificial CSF (ACSF) (in mm: NaCl 124, KCL 3, NaH2PO4 1.2, MgSO4 1.2, CaCl2 2, NaHCO3 26) or ACSF alone is injected by hand (over 60 s) using a 10 μl Hamilton syringe and PE10 tubing connected to a 30-gauge stainless steel injector. Mice are returned to the home cage until behavioral testing. Animals with misplaced or plugged cannula are excluded from the analyses.

Corticosterone Radioimunnoassay

Blood is collected via submandibular gland bleed. For stress measurements, collections occurred 30 min following swim stress (10 min). For baseline measurements samples are taken from mice in the home cage. All collections occurred between 10:00-11:00 A.M. Serum is isolated and corticosterone levels are determined using a radioimmunoassay (MP Biomedical).

Statistical Analysis

Values are expressed as mean±SEM. t test is used to assess significance in experiments comparing 2-groups. For experiments comprised of multiple factors a two-way ANOVA, with test for interaction, is used (SPSS). One-way ANOVA is used for single factor experiments involving more than two groups. For ANOVA results, planned contrast testing is used to test relationships hypothesized a priori between groups. p values (two-tailed) $<0.05$ are considered significant.

Results

Inhibiting ASIC1a with Triol in mice produces decreased levels of depression-like behavior in the forced swim test, the tail suspension test, and following unpredictable mild stress. Pharmacologically inhibiting ASIC1a with Triol also produces decreased levels of depression-like behavior in the forced swim test. The effects of ASIC1a inhibition with Triol in the forced swim test are independent of and additive to those of several commonly used antidepressants.

Example 3: Treatment of Pain

Activation of ASIC1a, ASIC3, and ASIC1a/2a have been strongly suggested to be implicated in pain sensation. Triol inhibits the above ASICs, so Triol has an analgesic effect. This study shows the analgesic activity of Triol. Experiments are performed on 12-week-old (20-25 g) C57BL/6J mice following the guidelines of the International Association for the Study of Pain. Inflammatory pain is evoked by intraplantar injection in the left hindpaw of 2% carrageenan (20 μl). After 2 h, Triol (12 mg/kg) or vehicle (20% HP-β-CD) is injected IV. The mechanical withdrawal threshold on the plantar surface of the hindpaw is measured with a set of von Frey hairs in the range of 0.4-26 gm (0.4, 1.2, 2, 4, 6, 8, 10, 15, 26 gm). The injection of Triol increases the latency for the paw withdrawal reflex.

Rat Pain Model

Male Sprague-Dawley rats (150-175 g) are acclimatized for a week before testing. Rats are housed in a controlled room with a 12-hour light/dark cycle, with free access to food and water. Rats are housed 4 per cage except after the bilateral implantation experiment (2 per cage and individually following surgery). Pain is induced by a single unilateral intra-articular injection of 50 μl complete Freund's adjuvant (CFA, heat-killed Mycobacterium 2 mg/ml) in the right hindpaw under isoflurane (4%) anaesthesia. Sham rats are injected with 50 μl of vehicle in the same conditions. Behavioral experiments are performed 14-16 days after pain induction, when rats weighed between 260 to 320 g.

Implantation and Microinjection of Triol into the Basolateral Amygdala of Sham and Pain Rats One week after pain induction, rats are deeply anesthetised with a mixture of xylazine hydrochloride (10 mg/kg) and ketamine (80 mg/kg). Stainless steel 26-gauge guide cannulas are both stereotaxically implanted. Guides are affixed onto the skull with photopolymerized cranioplastic cement. Until the microinjections, guide cannulas are occluded with dummy cannulas to maintain their patency. At least 7 days after the surgery, bilateral microinjections are performed through injection cannulas, that extended 1 mm beyond the guide cannula, connected to an Hamilton syringe preloaded with specific ASIC1a-containing channel peptide inhibitors, i.e., synthetic Triol (0.05 μg-11 pmoles/side), a specific blocker of homomeric ASIC1a, ASIC1a/2a, and probably heteromeric ASIC1a/ASIC2b channels 21,53, or synthetic mambalgin-1 (0.065 μg-10 pmoles/ side), another specific inhibitor with a broader pharmacological profile than Triol including homomeric ASIC1a and heteromeric ASIC1a/ASIC2b plus ASIC1a/ASIC2a channels or saline. Compounds are manually delivered (0.5 μl over 60 s) into the BLA in moderately anesthetized rats (1.5% isoflurane inhalation). The injection cannula is left in place for an additional minute to prevent any drug backflow. At the end of the pharmacological experiments, when rats are killed for immunohistochemistry or biopsy punch, the needle track is verified under a binocular microscope to confirm the infusion site.

Pharmacological Experiments

The effect of Triol (0.05 μg/0.5 μl/side) 15 min before the behavioral tests is evaluated in sham and Pain rats, 14 to 16 days following pain induction. The behavior of each rat is then assessed in the different tests (i.e., social interaction or elevated plus maze for anxiety, and paw pressure or paw immersion for pain, see below). To confirm the specificity of the effect observed following administration of Triol, the study also assesses the effect of administration of saline or mambalgin-1 (0.065 μg-10 pmoles/side), 15 min before paw pressure test for pain and the elevated plus maze for anxiety, in sham and Pain rats, 14 to 16 days following pain induction.

Mechanical hypersensitivity in sham and Pain animals is assessed with an analgesiometer (paw pressure test). Nociceptive thresholds are measured by applying increased pressure to the ipsilateral ankle of unrestrained rats until a vocalisation is obtained. The analgesiometer could be used to assess withdrawal, which is considered to be spinally mediated and as any withdrawal reflex could be affected by several factors such as motor impairment. Vocalization threshold, which is considered to be more supraspinally mediated and integrated, can be more accurate to assess pain behavior and sensitivity to analgesic treatments. Treatments are administered after measurement of two consecutive stable nociceptive (i.e., vocalization) threshold values that differ by not more than 10%, with at least a 10 min interval between two measurements. Vocalization threshold is assessed at baseline and 15, 25 and 45 min following Triol, mambalgin-1 or saline administration.

Results

Inhibiting ASIC1a with Triol in rats produces decreased levels of pain-related behavior in vocalization and mechanical hypersensitivity tests. The effects of ASIC1a inhibition with Triol in the pain tests are independent of and additive to those of several commonly used pain relief drugs.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The description herein is for the purpose of teaching the person of ordinary skill in the art how to practice the embodiments of the present application, and it is not intended to detail all those obvious modifications and variations of it which will become apparent to the skilled worker upon reading the description. It is intended, however, that all such obvious modifications and variations be included within the scope of the embodiments of the present application, which is defined by the following claims. The claims are intended to cover the components and steps in any sequence which is effective to meet the objectives there intended, unless the context specifically indicates the contrary.

What is claimed is:

1. A method of treating or reducing depression in a subject in need thereof comprising administering to a subject in need thereof a therapeutically effective amount of a pharmaceutical composition comprising triol, with a and a pharmaceutically acceptable carrier.

2. The method of claim 1, wherein the depression is a unipolar disorder.

3. The method of claim 1, wherein the triol is packaged for delivery in a titratable dosage form.

4. The method of claim 1, wherein the triol is packaged such that delivery is targeted to an area selected from the group consisting of: sublingual; buccal; parenteral; oral; rectal; nasal; and the pulmonary system.

5. The method of claim 1, wherein the triol is in the form selected from the group consisting of: gel; gel spray; tablet; liquid; capsule and for vaporization.

6. The method of claim 1, further comprising administering to the patient in need thereof a therapeutically effective amount of one or more other medicinal substances.

7. The method of claim 1, wherein said triol is administered to said subject orally, nasally, intrathecally, and/or intravenously.

* * * * *